US006579522B1

(12) United States Patent
Brough et al.

(10) Patent No.: US 6,579,522 B1
(45) Date of Patent: Jun. 17, 2003

(54) REPLICATION DEFICIENT ADENOVIRAL TNF VECTOR

(75) Inventors: Douglas E. Brough, Olney, MD (US); C. Richter King, Washington, DC (US); Imre Kovesdi, Rockville, MD (US); Jasper J. Schaible, Arlington, VA (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/604,694

(22) Filed: Jun. 27, 2000

(51) Int. Cl.[7] .......................... A01N 63/00; A61K 48/00
(52) U.S. Cl. ................... 424/93.2; 435/320.1; 435/455; 435/456; 514/44
(58) Field of Search ............................. 435/320.1, 455, 435/456; 514/44; 424/93.2

(56) References Cited

U.S. PATENT DOCUMENTS

| | | | |
|---|---|---|---|
| 4,879,226 A | 11/1989 | Wallace et al. ............... 435/68 |
| 5,206,152 A | 4/1993 | Sukhatme .................. 435/67.1 |
| 5,571,797 A | 11/1996 | Ohno et al. .................... 514/44 |
| 5,612,318 A | 3/1997 | Weichselbaum et al. ...... 514/44 |
| 5,624,830 A | 4/1997 | Mullen et al. ........... 435/172.3 |
| 5,641,755 A | 6/1997 | Weichselbaum et al. ...... 514/44 |
| 5,652,353 A | 7/1997 | Fiers et al. ................. 536/23.5 |
| 5,763,209 A | 6/1998 | Sukhatme .................... 435/69.1 |
| 5,770,581 A | 6/1998 | Weichselbaum et al. ...... 514/44 |
| 5,817,636 A | 10/1998 | Weichselbaum et al. ...... 514/44 |
| 5,851,806 A | 12/1998 | Kovesdi et al. .......... 435/91.41 |
| 5,962,424 A | 10/1999 | Hallahan et al. ............... 514/44 |
| 5,968,735 A | 10/1999 | Stein et al. ..................... 435/6 |
| 6,281,010 B1 * | 8/2001 | Gao et al. ................... 435/325 |
| 6,337,338 B1 * | 1/2002 | Kozlowski et al. .......... 514/311 |

FOREIGN PATENT DOCUMENTS

| | | |
|---|---|---|
| DE | 197 47 718 A1 | 5/1999 |
| EP | 0 486 526 B1 * | 8/1990 |
| EP | 0 869 180 A1 | 10/1998 |
| WO | WO 92/11033 | 7/1992 |
| WO | WO 94/06916 | 3/1994 |
| WO | WO 95/06120 | 3/1995 |
| WO | WO 95/34671 | 12/1995 |
| WO | WO 96/27021 | 9/1996 |
| WO | WO 96/33746 | 10/1996 |
| WO | WO 97/12623 A | 4/1997 |
| WO | WO 97/20051 A | 6/1997 |
| WO | WO 98/00166 | 1/1998 |
| WO | WO 98/46779 | 10/1998 |
| WO | WO 98/46781 | 10/1998 |
| WO | WO 98/55622 | 12/1998 |
| WO | WO 99/00518 | 1/1999 |
| WO | WO 99/21589 | 5/1999 |
| WO | WO 99/23216 | 5/1999 |
| WO | WO 99/46371 | 9/1999 |
| WO | WO 99/47690 | 9/1999 |
| WO | WO 99/55831 | 11/1999 |
| WO | WO 99/65515 | 12/1999 |

OTHER PUBLICATIONS

Karp et al. The Journal of Immunology, vol. 149, pp. 2076–2081, 1992.*
MA Morsy et al.,Proc.Natl.Acad.Sci USA, "An adenoviral vector deleted for all viral coding sequences results in enhanced safety and extended expression of a leptin transgene," Jul. 1998, vol. 95, pp. 7866–7871.*
Y Manome et al., Human Gene Therapy, "Transgene Expression in Malignant Glioma Using a Replication–Defective Adenoviral Vector Containing the Egr–1 Promoter: Activation by Ionizing Radiation or Uptake of Radioactive Iododeoxyuridine,"Jul. 1998, 9:1409–1417.*
RG Vile et al., Gene Therapy, "Cancer gene therapy:hard lessons and new courses," 2000, 7, pp. 2–8.*
J Gomez–Navarro et al., European Journal of Cancer, Gene Therapy for Cancer, Jun. 1999, vol. 35, No. 6, pp. 867–885.*
WF Anderson, Nature, "Human gene therapy," Apr. 1998, vol. 392, pp. 25–30.*
IM Verma et al., Nature, "Gene therapy–promises, problems and prospects," Sep. 1997, vol. 389, pp. 239–241.*
Walther et al., Viral Vector for Gene Transfer, Aug., Drugs 2000, vol. 60, No. 2, pp. 249–271.*
Mountain et al. Gene therpy: the first decade, Mar. 2000, TIBTECH, vol. 18, pp. 119–131.*
Kawashita et al., Regression of Hepatocellular Carcinoma in Vitro and in Vivo by Radiosensitizing Suicide Gene Therapy under the Inducible and Spatial Control of Radiation, Jun. 10, 1999, Human Gene Therapy, vol. 10, pp. 1509–1519.*
Mauceri et al., C. R. Acad. Sci. Series III, 322 (2–3), 225–228 (Feb. 1999).
Blankenstein et al., *J. Exp. Med.*, 173, 1047–1052 (1991).
Block et al., *Arch. Surg.*, 127, 1330–1334 (1992).
Brough et al., *J. Virol.*, 70 (9), 6497–6501 (1996).
Eggermont et al., *Annals of Surgery*, 224 (6), 756–765 (1996).
Chung et al., *Cancer Gene Therapy*, 5 (6), 344–349 (1998).
Fiers et al., *Proceedings of the American Association for Cancer Research*, 34, 581–582 (1993).
Fujii et al., *Blood*, 93 (12), 4328–4335 (1999).

(List continued on next page.)

Primary Examiner—Scott D. Priebe
Assistant Examiner—Brian Whiteman
(74) Attorney, Agent, or Firm—Leydig, Voit & Mayer, Ltd.

(57) ABSTRACT

An adenoviral vector comprising (a) an adenoviral genome deficient in the E4 region of the adenoviral genome, (b) a nucleic acid sequence coding for TNF, and (c) a radiation inducible promoter operably linked to the nucleic acid sequence coding for TNF. This invention also provides an adenoviral vector comprising (a) an adenoviral genome deficient in the E4 region of the adenoviral genome, (b) a nucleic acid sequence coding for TNF, and (c) a spacer element of at least 15 base pairs in the E4 region of the adenoviral genome. A method of producing an adenoviral vector and a method of treating a tumor or cancer in a host comprising administering an anti-cancer or anti-tumor effective amount of the adenoviral vector of the present invention also is provided.

17 Claims, 3 Drawing Sheets

OTHER PUBLICATIONS

Ginsberg et al., *Bulletin of the New York Academy of Medicine,* 73 (1), 53–58 (1996).
Hallahan et al., *Nature Medicine,* 1 (8), 786–791 (1995).
Hallahan et al., *Proceedings of ASCO,* 15, p. 84, Abstract 3, (1996).
Hersh et al., *Gene Therapy,* 2, 124–131 (1995).
Hu et al., *Cancer Research,* 57, 3339–3343 (1997).
Isobe et al., *Biochem. Biomed. Res. Comm.,* 202 (3), 1538–1542 (1994).
Jones et al., *Progress in Growth Factor Research,* 1, 107–122 (1989).
Jones et al., *Cancer Surveys,* 8 (4), 817–836 (1989).
Koshita et al., *Int. J. Cancer,* 63, 130–135 (1995).
Lejeune, *European J. Cancer,* 31A (6), 1109–1016 (1995).
Manusama et al., *Seminars in Surgical Oncology,* 14, 232–237 (1998).
Marr et al., *Cancer Gene Therapy,* 6 (5), 465–474 (1998).
Marr et al., *Int. J. Onconology,* 12, 509–515 (1998).
Marr et al., *Gene Therapy,* 4, 1181–1188 (1997).
Martinet et al., *Am. J. Respir. Cell Mol. Biol.,* 6, 510–515 (1992).
Mauceri et al., *Proceedings of the American Association for Cancer Research,* 37, p. 347, Abstract 2365, (1996).
Mauceri et al., *Cancer Research,* 56, 4311–4314 (1996).
Mauceri et al., *Radiation Oncology Investigations,* 5, 220–226 (1997).
Mulé, *Proceedings of the American Association for Cancer Research,* 34, 581 (1993).
Porter, *Trends in Biotechnology,* 9, 158–162 (1991).
Richards et al., *Annals of the New York Academy of Sciences,* 762, 282–293 (1995).
Sato et al., *Cancer Research,* 58, 1677–1683 (1998).
Seung et al., *Cancer Research,* 55, 5561–5565 (1995).
Slesarev et al., *Medical Oncology,* 15, 37–43 (1998).
Sparmann et al., *Int. J. Cancer,* 59, 103–107 (1994).
Spriggs et al., in: *Tumor Necrosis Factors: The Molecules and Their Emerging Role in Medicine,* Chapter 25, 383–406 (Raven Press, Ltd., New York, NY, 1992).
Staba et al., *Gene Therapy,* 5, 293–300 (1998).
Standiford et al., *Human Gene Therapy,* 10, 899–909 (1999).
Wakabayashi et al., *Neruol. Med. Chir. (Tokyo),* 37, 739–746 (1997).
Weichselbaum et al., *Cancer Research,* 54, 4266–4269 (1994).
Whartenby et al., *Drugs,* 50 (6), 951–958 (1995).
Wright et al., *Cancer Gene Therapy,* 5 (6), 371–379 (1998).

* cited by examiner

REPLICATION DEFICIENT ADENOVIRAL TNF VECTOR

TECHNICAL FIELD OF THE INVENTION

This invention pertains to a replication deficient adenoviral vector comprising a nucleic acid sequence coding for tumor necrosis factor (TNF), as well as a method of constructing and using such vector.

BACKGROUND OF THE INVENTION

Tumor necrosis factor (TNF), especially TNF-α, is well-known for its anti-tumor effects and ability to act synergistically with radiation therapy. For example, certain replication deficient adenoviral vectors comprising the TNF-α gene have been used in conjunction with radiation therapy to treat tumors in animals with some success (e.g., Hallahan et al., *Nat. Med.*, 1, 786–91 (1995)). The use of TNF as an anti-cancer/anti-tumor agent, however, has been limited by its severe systemic effects.

There remains a need for replication deficient TNF adenoviral vectors that have greater flexibility in their construction and use, and can provide greater success in the treatment of a tumor or cancer. The present invention provides such a vector, as well as a method of constructing such vector, and a therapeutic method involving the use of such vector.

BRIEF SUMMARY OF THE INVENTION

The present invention provides an adenoviral vector comprising (a) an adenoviral genome deficient in the early growth-4 (E4) region of the adenoviral genome, (b) a nucleic acid sequence coding for TNF, and (c) a radiation inducible promoter operably linked to the nucleic acid sequence coding for TNF. This invention also provides an adenoviral vector comprising (a) an adenoviral genome deficient in the E4 region of the adenoviral genome, (b) a nucleic acid sequence coding for TNF, and (c) a spacer element of at least 15 base pairs in the E4 region of the adenoviral genome.

A method of producing an adenoviral vector also is provided by the present invention comprising (a) providing an adenoviral genome that is deficient in the E4 region of the adenoviral genome, (b) inserting a nucleic acid sequence coding for TNF into the adenoviral genome, and (c) inserting a radiation-inducible promoter into the adenoviral genome such that it is operably linked to the nucleic acid sequence coding for TNF. This invention further provides a method of treating a tumor or cancer in a host comprising administering an anti-cancer or anti-tumor effective amount of the adenoviral vector of the present invention to a host in need thereof.

The present invention may best be understood with reference to the accompanying drawings and in the following detailed description of the preferred embodiments.

DETAILED DESCRIPTION OF THE INVENTION

Figure 1A:
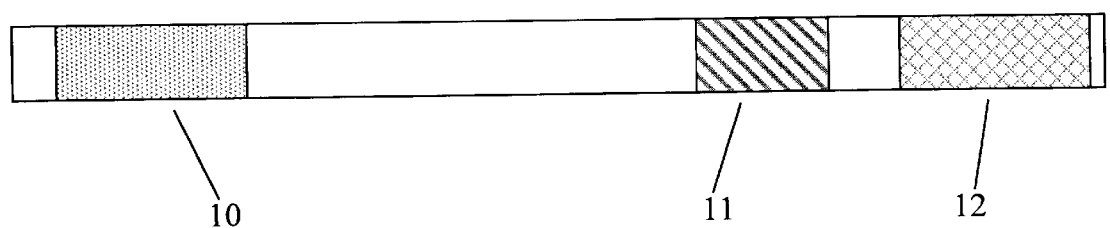
FIG. 1A is a schematic representation of a vector containing an unmodified adenoviral genome.

The present invention provides an adenoviral vector comprising (a) an adenoviral genome deficient in the E4 region of the adenoviral genome, (b) a nucleic acid sequence coding for TNF, and (c) a radiation inducible promoter operably linked to the nucleic acid sequence coding for TNF. The present invention also provides an adenoviral vector comprising (a) an adenoviral genome deficient in the E4 region of the adenoviral genome, (b) a nucleic acid sequence coding for TNF, and, (c) a spacer element of at least 15 base pairs in the E4 region of the adenoviral genome.

Adenoviral Genome

Any subtype mixture of subtypes, or chimeric adenovirus can be used as the source of the viral genome for generation of an adenoviral vector in conjunction with the present invention. Preferably the genome of a human serotype adenovirus is used, such as a type 2 (Ad2) or type 5 (Ad5) adenoviral genome. Although any suitable adenoviral genome can be used in conjunction with the present invention, the Ad5 adenoviral genome is most preferred, and the present invention is described further herein with respect to the Ad5 serotype.

The adenoviral genome used in conjunction with the present invention is desirably replication deficient. A deficiency in a gene, gene function, or gene or genomic region, as used herein, is defined as a deletion of sufficient genetic material of the viral genome to impair or obliterate the function of the gene whose nucleic acid sequence was deleted in whole or in part and to provide room in, or capacity of, the viral genome for the insertion of a nucleic acid sequence that is foreign to the viral genome. Such a deficiency can be in a gene or genome region essential or unessential for propagation of the adenoviral vector in a non-complementing cellular host. A deficiency in an adendviral genome region essential for such propagation (e.g., early region 1 (E1), early region 2A (E2A), early region 2B (E2B), early region 4 (E4), late region 1 (L1), late region 2 (L2), late region 3 (L3), late region 4 (L4), and late region 5 (L5)) renders an adenoviral vector based on that adenoviral genome replication deficient.

The adenoviral vector of the present invention desirably is multiply replication deficient, i.e., it is deficient in at least two genome regions required for viral propagation in a non-complementing cellular host (i.e., viral replication in vitro). Such regions include the E1, E2, E4, or L1–L5 regions. Even though the E1 region can be considered as consisting of early region 1A (E1A) and early region 1B (E1B), a deficiency in either or both of the E1A and/or E1B regions is considered as a single deficiency in the context of the present invention. In addition, such a vector can be deficient in one or more regions that are not required for viral propagation, e.g., the vectors can be additionally deficient in early region 3 (E3).

The present inventive adenoviral vector desirably is deficient in the E1 and E4 regions, preferably with the entire coding region of the E4 region having been deleted from the adenoviral vector. In the context of the present invention, the coding region refers to the portion or portions of a genomic region that encode a protein product (e.g., the open reading frames (ORFs) of the E4 region). Thus, a vector in which the entire coding region of the E4 region of the adenoviral genome has been deleted is lacking all of the ORFs of that region. The E4 region of the present inventive adenoviral vector preferably retains the native E4 promoter, polyadenylation sequence, and/or the right-side inverted terminal repeat (ITR).

The adenoviral vector of the present invention also can be deficient in one or more additional regions required for viral propagation (especially other early regions required for viral propagation, such as the E2A and/or E2B regions). More preferably, the E3 region of the adenoviral genome also is removed. Thus, preferred configurations of the present inventive adenoviral vector include (a) E1⁻E4⁻, (b) E1⁻E2A⁻E4⁻, and (c) E2A⁻E4⁻ adenoviral vectors, any of which also can be E3⁻.

Figure 1B:
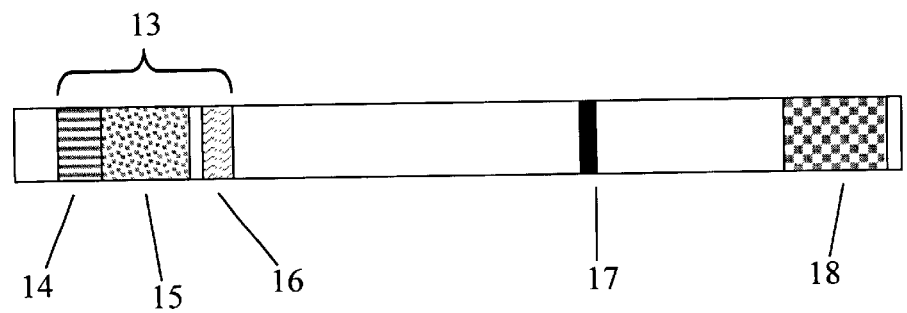
FIG. 1B is a schematic representation of a vector containing a modified adenoviral genome and the genetic elements in accordance with the present invention.

FIG. 1A provides a schematic representation of the Ad5 genome. FIG. 1B is a schematic representation of an exemplary adenoviral vector, which figure shows, by comparison to the unaltered Ad5 adenoviral genome represented by FIG. 1A, that (i) the E1 region (10) has been replaced by a radiation inducible promoter (14), a nucleic acid sequence encoding TNF (15), and a polyadenylation sequence (16), (ii) the E3 region (11) has been deleted (17), and (iii) the coding region of the E4 region (12) has been replaced by a spacer element (18), thereby creating a vector deficient in the E1, E3, and E4 regions.

If the adenoviral vector of the present invention is deficient in the E2A region, the vector preferably further comprises a portion of the E2A region of the adenoviral genome in the E2A deficient region, which is less than about 230 base pairs in length. Generally, the E2A region of the adenovirus codes for DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., *Virology*, 196, 269–281 (1993)). While deletions in the E2A region coding for the Ct region of the DBP have no effect on viral propagation, deletions in the E2A region which code for amino acids 2 to 38 of the Nt domain of the DBP impair viral propagation. Therefore, it is preferable that any multiply replication deficient adenoviral vector contain this portion of the E2A region of the adenoviral genome.

In particular, for example, the desired portion of the E2A region to be retained is that portion of the E2A region of the adenoviral genome which is defined by the 5' end of the E2A region, specifically, positions Ad5(23816) to Ad5(24032) of the E2A region of the adenoviral genome of serotype Ad5. This portion of the adenoviral genome desirably is included in the adenoviral vector because it is not complemented in current E2A cell lines, and in its absence the requisite levels of viral propagation and fiber expression cannot be obtained in complementing cell lines.

The present invention is not limited to adenoviral vectors that are deficient in gene functions only in the early region of the genome. Also included are adenoviral vectors that are deficient in the early and late regions of the genome, as well as vectors in which essentially the entire genome has been removed, in which case it is preferred that at least either the viral ITRs and some of the promoters or the viral ITRs and a packaging signal are left intact. One of ordinary skill in the art will appreciate that the larger the region of the adenoviral genome that is removed, the larger the piece of exogenous nucleic acid sequence that can be inserted into the genome. For example, given that the adenoviral genome is 36 kb, by leaving the viral ITRs and some of the promoters intact, the capacity of the adenovirus is approximately 35 kb. Alternatively, one could generate a multiply deficient adenoviral vector that contains only the ITR and a packaging signal. This could then effectively allow for expression of 37–38 kb of foreign nucleic acid sequence from this vector. Of course, the inclusion of a spacer element in any or all of the deficient adenoviral regions will decrease the capacity of the adenoviral vector in size corresponding with the size of the spacer element sequence.

Nucleic Acid Sequence Encoding TNF

Preferably, the vector comprises at least one expression cassette which includes (i.e., comprises) a nucleic acid sequence coding for TNF. Nucleic acid sequences encoding TNF include nucleic acid sequences encoding any member of the TNF family of proteins. The adenoviral vector of the present invention preferably comprises a nucleic acid sequence coding for TNF-α. A nucleic acid sequence coding for TNF is described in detail in U.S. Pat. No. 4,879,226, which discloses a nucleic acid sequence encoding a "human TNF, in mature form, secreted from host cells" (see column 7, lines 26–28), as set forth in SEQ ID NO: 2.

The nucleic acid sequence coding for TNF is preferably located in the E1 region (e.g., replaces the E1 region in whole or in part, preferably in whole) of the adenoviral genome. For example, the E1 region can be replaced by a promoter-variable expression cassette comprising a nucleic acid sequences encoding TNF. The term "expression cassette," as used herein, refers to any nucleic acid sequence that can be inserted into the adenoviral genome to produce a foreign gene product. For example, as shown in FIGS. 1A and 1B, the E1 region (10) can be replaced by an expression cassette (13) comprising a radiation inducible promoter (14), a nucleic acid sequence encoding TNF (15), and a polyadenylation sequence (16). In addition to the expression cassette comprising the nucleic acid sequence encoding TNF, the vector can comprise other expression cassettes containing nucleic acid sequences encoding other products, which cassettes can replace any of the deleted regions of the adenoviral genome. The insertion of an expression cassette into the adenoviral genome (e.g., the E1 region of the genome) can be facilitated by known methods, for example, by the introduction of a unique restriction site at a given position of the adenoviral genome.

Preferably, the nucleic acid sequence encoding TNF further comprises a transcription-terminating region such as a polyadenylation sequence located 3' of the region encoding TNF. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus). A preferred polyadenylation sequence is the SV40 (Human Sarcoma Virus-40) polyadenylation sequence.

Preferably, the nucleic acid sequence encoding TNF is operably linked to (i.e., under the transcriptional control of) one or more promoter and/or enhancer elements, for example, as part of a promoter variable expression cassette. Techniques for operably linking sequences together are well known in the art. Any suitable promoter or enhancer sequence can be used in conjunction with the present invention. Suitable promoters and enhancer sequences are generally known in the art. Preferred vectors according to the present invention comprise a radiation-inducible promoter operably linked to a nucleic acid sequence encoding TNF. The use of a radiation inducible promoter provides control over transcription of the foreign gene product, for example, by the administration of radiation to a cell or host comprising the adenoviral vector. Any suitable radiation inducible promoter can be used in conjunction with the present invention. Suitable radiation inducible promoters are generally known in the art. A preferred radiation inducible promoter for use in conjunction with the present invention is the early growth region-1 (Egr-1) promoter, specifically the CArG domain of the Egr-1 promoter. The Egr-1 promoter has been described in detail in U.S. Pat. No. 5,206,152 and International Patent Application WO 94/06916. The promoter can be introduced into the foreign genome by methods known in the art, for example, by the introduction of a unique restriction site at a give region of the genome. Alternatively, the promoter can be inserted as part of the expression cassette comprising the nucleic acid sequence coding for TNF.

Spacer Element

The present inventive adenoviral vector, when multiply replication deficient, preferably includes a spacer element to provide viral growth in a complementing cell line similar to that achieved by singly replication deficient adenoviral vectors, particularly a singly replication deficient E1⁻ adenoviral vector. In the absence of a spacer, production of fiber protein and/or viral growth of the multiply replication deficient adenoviral vector is reduced by comparison to that of a singly replication deficient adenoviral vector. However, inclusion of the spacer in at least one of the deficient adenoviral regions, preferably the E4 region as shown in FIG. 1B (18), counteracts this defect in growth and fiber expression.

In the preferred E4⁻ adenoviral vector of the present invention wherein the L5 fiber region is retained, the spacer is desirably located between the L5 fiber region and the right-side ITR. More preferably, in such an adenoviral vector, the E4 polyadenylation sequence alone or, most preferably, in combination with another sequence, exists between the L5 fiber region and the right-side ITR, so as to sufficiently separate the retained L5 fiber region from the right-side ITR, such that viral production of such a vector approaches that of a singly replication deficient adenoviral vector, particularly a singly replication deficient E1⁻ adenoviral vector. The use of a spacer in an adenoviral vector is described in U.S. Pat. No. 5,851,806.

As the function of the replication deficient region of the genome can be provided by a complementing cell line, the spacer element does not need to provide the deficient function and can be any sequence. Thus, the spacer element is limited only by the size of the insert that the vector will accommodate. The spacer element can be of any suitable size, desirably at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs.

The spacer element can contain any sequence or sequences which are of the desired length. The spacer element sequence can be coding or non-coding and native or non-native with respect to the adenoviral genome, but does not restore the replication function td the deficient region. The spacer element can also contain a promoter-variable expression cassette. More preferably, the spacer element comprises an additional polyadenylation sequence and/or a foreign gene. Preferably, in the case of a spacer element inserted into a region deficient for E4, both the E4 polyadenylation sequence and the E4 promoter of the adenoviral genome or any other (cellular or viral) promoter remain in the vector. In such an embodiment, the spacer element is located between the E4 polyadenylation site and the E4 promoter, or, if the E4 promotor is not present in the vector, the spacer element is proximal to the right-side ITR.

The spacer element can comprise any suitable polyadenylation sequence. Examples of suitable polyadenylation sequences include synthetic optimized sequences, as well as the polyadenylation sequences of BGH (Bovine Growth Hormone), polyoma virus, TK (Thymidine Kinase), EBV (Epstein Barr Virus), and the papillomaviruses, including human papillomaviruses and BPV (Bovine Papilloma Virus). Preferably, particularly in the E4 deficient region, the spacer element includes an SV40 (Human Sarcoma Virus-40) polyadenylation sequence. The SV40 polyadenylation sequence allows for higher virus production levels of multiply replication deficient adenoviral vectors.

A foreign gene also can function as the spacer element in the E4 deficient region of the adenoviral genome. The foreign gene is limited only by the size of the fragment the vector can accommodate and can be any suitable gene. Examples of suitable foreign genes include marker gene sequences such as pGUS, secretory alkaline phosphatase, luciferase, B-galactosidase, and human anti-trypsin; therapeutic genes; potential immune modifiers such as B3–19K, E3–14.7, ICP47, fas ligand gene, and CTLA4 genes; biologically inactive sequences (e.g. sequences that will not be transcribed to produce a product or which encode a defective or biologically inactive product), and other innocuous sequences such as the glucuronidase gene.

Vector Construction

The present invention provides a method of producing an adenoviral vector comprising (a) providing an adenoviral genome that is deficient in the E4 region of the adenoviral genome, (b) inserting a nucleic acid sequence coding for TNF into the adenoviral genome, and (c) inserting a radiation-inducible promoter into the adenoviral genome such that it is operably linked to the nucleic acid sequence coding for TNF. The present invention also provides a method of producing an adenoviral vector comprising (a) providing an adenoviral genome that is deficient in the E4 region of the adenoviral genome, (b) inserting a nucleic acid sequence coding for TNF into the adenoviral genome, and (c) inserting a spacer element into the E4 region of the adenoviral genome. As those of ordinary skill in the art will appreciate, the method provided by the present invention can include other steps or elements, such as the insertion of other nucleic acid sequences into, or deletion of such sequences from, the adenoviral genome used to provide the adenoviral vector. Furthermore, the various aspects of the present inventive method (e.g., the adenoviral genome, nucleic acid sequences coding for TNF, radiation inducible promoter, spacer element, etc.) are as previously described herein with respect to the adenoviral vector of the present invention.

The present inventive method of producing an adenoviral vector can be carried out using techniques known to those of ordinary skill in the art. In general, virus vector construction relies on the high level of recombination between adenoviral nucleic acid sequences in a cell. Two or three separate adenoviral nucleic acid sequences (e.g., DNA fragments), containing regions of similarity (or overlap) between sequences and constituting the entire length of the genome, are transfected into a cell. The host cell's recombination machinery constructs a full-length viral vector genome by recombining the aforementioned seqences. Other suitable procedures for constructing viruses containing alterations in various single regions have been previously described (Berkner et al., *Nucleic Acids Res.*, 12, 925–941 (1984); Berkner et al., *Nucleic Acids Res.*, 11, 6003–6020 (1983); Brough et al., *Virol.*, 190, 624–634 (1992)) and can be used to construct multiply deficient viruses; yet other suitable procedures include, for example, in vitro recombination and ligation.

A preferred method of constructing the present inventive adenoviral vector first involves constructing the necessary deletions or modifications (such as adding a spacer element to a deleted region) of a particular region of the adenoviral genome. Such modifications can be performed, for example, in a plasmid cassette using standard molecular biological techniques. The altered nucleic acid sequence (containing the deletion or modification) then is moved into a much larger plasmid that contains up to one-half of the adenovirus genome to provide a base plasmid comprising the modified adenoviral genome. The next step is to insert an expression cassette into a desired region of the modified adenoviral genome. The expression cassette can be provided by standard methods known in the art, for example, by isolating the cassette from a plasmid. The isolated cassette then can be transfected with the plasmid DNA (containing the modified adenoviral genome) into a recipient cell. The plasmid is, optionally, linearized prior to transfection by digestion with a suitable restriction enzyme to facilitate the insertion of the expression cassette at a desired position in the adenoviral genome. Selection of a suitable restriction enzyme is well within the skill of the ordinary artisan. The two pieces of DNA recombine to form a plasmid comprising the modified adenoviral genome and the expression cassette. The plasmid is isolated from the host cell and introduced into recipient cell that complements for the missing viral functions of the recombined viral genome to produce the adenoviral vector comprising the modified viral genome and the expression cassette. The vector can be further modified by alteration of the ITR and/or packaging signal.

Complementing Cell Lines

Complementing cell lines for propagation or growth of the present inventive replication deficient adenoviral vectors are known and described in detail in U.S. Pat. No. 5,851,806 and Brough et al., *Virol.*, 70, 6497–6501 (1996). The preferred cell lines are characterized in complementing for at least one gene function of the gene functions comprising the E1, E2, and E4 regions of the adenoviral genome. Other cell lines include those that complement adenoviral vectors that are deficient in at least one gene function from the gene functions comprising the late regions, those that complement for a combination of early and late gene functions, and those that complement for all adenoviral functions. One of ordinary skill in the art will appreciate that the cell line of choice is one that specifically complements for those functions that are missing from the recombinant replication deficient adenoviral vector of interest and that are generated using standard molecular biological techniques. The cell lines are further characterized in that they contain the complementing genes in a non-overlapping fashion, which minimizes, and practically eliminates, the possibility of the vector genome recombining with the cellular DNA. Accordingly, replication competent adenoviruses are not present in vector stocks, which are, therefore, suitable for certain therapeutic purposes, especially gene therapy purposes. This also avoids the replication of the adenoviruses in non-complementing cells.

The complementing cell line must be one that is capable of expressing the products of the deficient adenoviral gene functions at the appropriate level for those products in order to generate a high titer stock of recombinant adenoviral vector. For example, it is necessary to express the E2A product, DBP, at stoichiometric levels, i.e., relatively high levels, for adenoviral DNA replication, but the E2B product, Ad pol, is necessary at only catalytic levels, i.e., relatively low levels, for adenoviral DNA replication. Not only must the level of the product be appropriate, the temporal expression of the product must be consistent with that seen in normal viral infection of a cell to assure a high titer stock of recombinant adenoviral vector. For example, the components necessary for viral DNA replication must be expressed before those necessary for virion assembly. In order to avoid cellular toxicity, which often accompanies high levels of expression of the viral products, and to regulate the temporal expression of the products, inducible promoter systems are used. For example, the sheep metallothionine inducible promoter system can be used to express the complete E4 region, the open reading frame 6 of the E4 region, and the E2A region. Other examples of suitable inducible promoter systems include, but are not limited to, the bacterial lac operon, the tetracycline operon, the T7 polymerase system, and combinations and chimeric constructs of eukaryotic and prokaryotic transcription factors, repressors, and other components. Where the viral product to be expressed is highly toxic, it is desirable to use a bipartite inducible system, wherein the inducer is carried in a viral vector and the inducible product is carried within the chromatin of the complementing cell line. Repressible/inducible expression systems, such as the tetracycline expression system and lac expression system also can be used.

Methods of Use

The present invention provides a method of treating a tumor or cancer in a host comprising administering an anti-cancer or anti-tumor effective amount of the adenoviral vector of the present invention to a host in need thereof.

One skilled in the art will appreciate that suitable methods of administering a replication deficient adenoviral vector of the present invention to an animal for therapeutic or prophylactic purposes, e.g., gene therapy, vaccination, and the like (see, for example, Rosenfeld et al., *Science*, 252, 431–434 (1991), Jaffe et al., *Clin. Res.*, 39(2), 302A (1991), Rosenfeld et al., *Clin. Res.*, 39(2), 311A (1991), Berkner, *BioTechniques*, 6, 616–629 (1988)), are available, and, although more than one route can be used to administer the vector, a particular route can provide a more immediate and more effective reaction than another route.

The present invention provides a pharmaceutical composition comprising the adenoviral vector of the present invention and a carrier, especially a pharmaceutically acceptable (e.g., a physiologically or pharmacologically acceptable) carrier (e.g., excipient or diluent). Pharmaceutically acceptable carriers are well-known to those who are skilled in the art and are readily available. The choice of carrier will be determined in part by the particular method used to administer the pharmaceutical composition. Accordingly, there is a wide variety of suitable formulations of the pharmaceutical composition of the present invention. The following formulations and methods are merely exemplary and are in no way limiting. However, oral, injectable and aerosol formulations are preferred.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The vectors of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the vectors employed in the present invention can be made into suppositories by mixing with a variety of bases such as emulsifying bases or watersoluble bases. Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the particular adenoviral vector, the composition containing the adenoviral vector, the method of administration, and the particular site and organism being treated. The dose should be sufficient to effect a desirable response, e.g., therapeutic or prophylactic response, within a desirable time frame.

The present method of treating a tumor or cancer in a host further can comprise the administration (i.e., pre-administration, co-administration, and/or post-administration) of other treatments and/or agents to modify (e.g., enhance) the effectiveness thereof. For example, an adenoviral vector of the present invention, particularly a vector comprising a nucleic acid sequence coding for TNF that is operably linked to a radiation inducible promoter, can be administered in conjunction with the administration of radiation. The radiation can be administered in any suitable manner, for example, by exposure to an external source of radiation (e.g., infrared radiation), or through the use of an internal source of radiation (e.g., through the chemical or surgical administration of a source of radiation). For instance, the adenoviral vector of the present invention can be used in conjunction with brachytherapy, wherein a radioactive source is placed (i.e., implanted) in or near a tumor to deliver a high, localized dose of radiation. Radiation is desirably administered in a dose sufficient to induce the production of a therapeutic level of TNF in the host.

The method of the present invention, additionally or alternatively to the administration of radiation, further can comprise the administration of other substances which locally or systemically alter (i.e., diminish or enhance) the effect of TNF in vivo. For example, substances that diminish the systemic effect of TNF can be used to control the level of systemic toxicity expressed in a host. Likewise, substances that enhance the local effect of TNF can be used to reduce the level of TNF required to produce a prophylactic or therapeutic effect in a host. Such substances include TNF antagonists, for example, soluble TNF receptors or anti-TNF antibodies, and TNF agonists. Other suitable antagonists, agonists, and other substances that alter the effect of TNF are available and generally known in the art.

The replication deficient adenoviral vectors of the present invention also have utility in vitro. For example, they can be used to study adenoviral gene function and assembly, the production of TNF, or the expression of other foreign nucleic acid sequences in a suitable target cell. One of ordinary skill can identify a suitable target cell by selecting one that can be transfected by the adenoviral vector, resulting in expression of the thereby inserted adenoviral nucleic acid sequence complement. Preferably, a suitable target cell is selected that has receptors for attachment and penetration of adenovirus into a cell. Such cells include, but are not limited to, those originally isolated from any mammal. Once the suitable target cell has been selected, the target cell is contacted with an adenoviral vector of the present invention, thereby effecting transfection or infection, respectively. Expression, toxicity, and other parameters relating to the insertion and activity of the nucleic acid sequence encoding TNF, or other foreign nucleic acid sequences, in the target cell then is measured using conventional methods well known in the art. For example, the adenoviral vector of the present invention can be used to study the interaction and targeting of TNF with respect to other cellular molecules. In so doing, researchers can learn and elucidate the phenomenology concerning adenoviral infection as well as the efficacy and effect of expression of various foreign nucleic acid sequences introduced by the adenoviral vector in various cell types that are explanted from various organisms and studied in tissue culture.

Moreover, cells explanted or removed from a patient having a disease that is suitably treated by gene therapy in the context of the present invention usefully are manipulated in vitro. For example, cells cultured in vitro from such an individual are placed in contact with an adenoviral vector of the present invention under suitable conditions to effect transfection, which are readily determined by one of ordinary skill in the art. Such contact suitably results in transfection of the vector into the cultured cells, where the transfected cells are selected using a suitable marker and selective culturing conditions. In so doing, using standard methods to test for vitality of the cells and thus measure toxicity and to test for presence of gene products of the foreign nucleic acid sequences of the vector of the present invention and thus measure expression, the cells of the individual are tested for compatibility with, expression in, and toxicity of the vector of the present invention, thereby providing information as to the appropriateness and efficacy of treatment of the individual with the vector system so tested. Such explanted and transfected cells, in addition to serving to test the potential efficacy/toxicity of a given gene therapy regime, also can be returned to an in vivo position within the body of the individual. Such cells so returned to the individual can be returned unaltered and unadorned except for the in vitro transfection thereof, or encased by or embedded in a matrix that keeps them separate from other tissues and cells of the individual's body. Such a matrix can be any suitable biocompatible material, including collagen, cellulose, and the like. Of course, alternatively or in addition, preferably after a positive response to the in vitro test, the transfection can be implemented in vivo by administration means as detailed hereinabove.

Further Aspects of the Present Invention

As those of ordinary skill in the art will appreciate, the adenoviral vector, and methods involving the same, provided by the present invention can comprise any combination or permutation of the elements described herein. A vector having a preferred configuration of such elements is schematically represented by FIG. 1B. Furthermore, a vector having such configuration of elements is provided by a vector that comprises, consists essentially of, or consists of the nucleic acid sequence of SEQ ID NO:1. However, many modifications and variations of the present illustrative nucleic acid sequence are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or nucleic acid sequence of a given gene and can be constructed by conventional synthetic or site-specific mutagenesis procedures. Synthetic DNA methods can be carried out tin substantial accordance with the procedures of Itakura et al., *Science*, 198, 1056–1063 (1977), and Crea et al., *Proc. Natl. Acad. Sci. USA*, 75, 5765–5769 (1978). Site-specific mutagenesis procedures are described in Maniatis et al., *Molecular Cloning: A Laboratory Manual*, Cold Spring Harbor, N.Y. (2d ed. 1989). Therefore, the present invention is in no way limited to the nucleic acid sequence specifically exemplified herein. Exemplified vectors are for gene therapy of tumors and/or cancer and, therefore, contain and express the TNF gene. However, the vectors described also can comprise genes used to treat other similar or different diseases and/or afflictions including, but not limited to, other chronic lung diseases, such as emphysema, asthma, adult respiratory distress syndrome, and chronic bronchitis, as well as coronary heart disease, and other afflictions suitably treated or prevented by gene therapy, vaccination, and the like. Accordingly, any gene or nucleic acid sequence can be inserted into the adenoviral TNF vector.

The adenoviral vector can be modified in other ways without departing from the scope and spirit of the present invention. For example, the coat protein of the present inventive adenoviral vector can be manipulated to alter the binding specificity or recognition of the virus for a viral receptor on a potential host cell. Such manipulations can include deletion of regions of the fiber, penton, or hexon, insertions of various native or non-native ligands into portions of the coat protein, and the like. Manipulation of the coat protein can broaden the range of cells infected by a viral vector or enable targeting of a viral vector to a specific cell type.

For example, the vector can comprise a chimeric coat protein (e.g., a fiber, hexon or penton protein), which differs from the wild-type (i.e., native) coat protein by the introduction of a nonnative amino acid sequence, preferably at or near the carboxyl terminus. Preferably, the nonnative amino acid sequence is inserted into or in place of an internal coat protein sequence. The resultant chimeric viral coat protein is able to direct entry into cells of the adenoviral vector comprising the coat protein that is more efficient than entry into cells of an adenoviral vector that is identical except for comprising a wild-type viral coat protein rather than the chimeric viral coat protein.

The chimeric virus coat protein desirably binds a novel endogenous binding site present on the cell surface. A result of this increased efficiency of entry is that the adenoviral virus can bind to and enter numerous cell types which a virus comprising wild-type coat protein typically cannot enter or can enter with only a low efficiency.

Alternatively, the adenoviral vector of the present invention can comprise a chimeric virus coat protein that is not selective for a specific type of eukaryotic cell. Such chimeric coat protein differs from the wild-type coat protein by an insertion of a nonnative amino acid sequence into or in place of an internal coat protein sequence. In a vector comprising a non-selective chimeric coat protein, the virus coat efficiently binds to a broader range of eukaryotic cells than a wild-type virus coat, such as described in International Patent Application WO 97/20051.

Specificity of binding of an adenovirus to a given cell also can be adjusted by use of an adenovirus comprising a short-shafted adenoviral fiber gene, as discussed in U.S. Pat. No. 5,962,311. Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenovirus to a given cell. Alternatively, use of an adenovirus comprising a short-shafted fiber enables targeting of the adenovirus to a desired cell-surface receptor by the introduction of a nonnative amino acid sequence either into the penton base or the fiber knob.

In addition, the ability of a viral vector to recognize a potential host cell can be modulated without genetic manipulation of the coat protein. For instance, complexing an adenovirus with a bispecific molecule comprising a penton base-binding domain and a domain that selectively binds a particular cell surface binding site enables one of ordinary skill in the art to target the vector to a particular cell type.

Many modifications to a viral vector, specifically an adenoviral vector, are known in the art. Suitable modifications for an adenoviral vector include those modifications described in U.S. Pat. Nos. 5,559,099; 5,731,190; 5,712,136; 5,770,442; 5,846,782; 5,926,311; and 5,965,541 and International Patent Applications WO 96/07734, WO 96/26281, WO 97/20051, WO 98/07865, WO 98/07877, and WO 98/54346.

The following examples further illustrate the present invention and, of course, should not be construed as in any way limiting its scope. Enzymes referred to in the examples are available, unless otherwise indicated, from Bethesda Research Laboratories (BRL), Gaithersburg, Md., New England Biolabs Inc. (NEB), Beverly, Mass., or Boehringer Mannheim Biochemicals (BMB), Indianapolis, Ind., and are used in substantial accordance with the manufacturer's recommendations. Many of the techniques employed herein are well known to those in the art. Molecular biology techniques are described in detail in suitable laboratory manuals, such as Maniatis et al., *Molecular Cloning: A Laboratory Manual*, Cold Spring Harbor, N.Y. (2d ed. 1989), and *Current Protocols in Molecular Biology* (Ausubel et al., eds. (1987)).

EXAMPLE 1

The following example demonstrates the preparation of an adenoviral vector in accordance with the present invention. A first plasmid (base plasmid) comprising a type-5 adenoviral genome was prepared having deficiencies in the E1, E3, and E4 regions, wherein the E3 region was entirely deleted and the E4 region comprised an SV40 polyadenylation sequence. A second plasmid (donor plasmid) was prepared comprising an expression cassette having an Egr-1 radiation-inducible promoter operably linked to a nucleic acid sequence encoding TNF-α. The donor plasmid was digested with Drd-I restriction endonuclease, and a nucleic acid segment of approximately 6.5 kbp comprising the Egr-I/TNF-α expression cassette was isolated by gel electrophoresis. The base plasmid was digested using Swa-I restriction endonuclease, and the linearized plasmid was de-phosphorylated. Competent *E. coli* BJIq cells were transformed with 50 ng of the 6.5 kbp (approx.) donor plasmid fragment and 50 ng of the linearized base plasmid. The transformed cells were plated on luria/SOC broth plates containing 50 $\mu g/\mu l$ of kanamycin and 50 $\mu g/\mu l$ tetracycline. The resulting colonies were screened for recombinants, and the positive recombinants were grown on luria broth/kanamycin plates.

The recombinant plasmid DNA was isolated from the transformed *E. coli* BJIq cells by standard techniques. Using standard procedures, the isolated plasmid DNA was linearized by digestion with Pac-I restriction endonuclease, and the linearized plasmid DNA was transfected in 293-ORF6 cells (derived from type 293 human embryonic kidney cells), which compliment for E1 and E4 deficiencies, to produce an adenoviral Egr-1/TNF-α E1⁻, E3⁻, E4⁻ vector having the sequence of SEQ ID NO:1.

EXAMPLE 2

The following example demonstrates the use of an adenoviral vector prepared in accordance with the present invention to treat or prevent tumors in a host.

Three treatment groups were established, each comprising eight nude mice having radio-resistant human squameous tumor cell line (SQ-20B) xenograft tumors. The first treatment group received a dose of $5\times10^{10}$ particle units (PU) of the adenoviral particles of Example 1 (in a total volume of 32 $\mu l$ with a viral buffer) by injection directly into the tumor tissue at five sites (four injections around the periphery of each tumor and one injection into the center of each tumor) at days 0, 4, 7, and 11. The second treatment group received the same doses of adenoviral vector administered in conjunction with exposure of the tumor to 5 Gy of infrared radiation on days 0–4 and 7–9 (totaling 40 Gy of radiation). The third treatment group received only the infrared radiation.

Significant tumor regression was observed in the first treatment group by day four, while no regression was observed in the second treatment group until day 11. At day 11, one animal in the first treatment group and three animals in the second treatment group had no visible tumor. After 62 days, all eight mice in the second treatment group were cured (i.e., no visible tumors were present), while six mice of the first group were cured, and only one mouse of the third group (no vector) was cured.

The results of this example demonstrate that an adenoviral vector according to the present invention can be successfully used to treat tumors in a host.

EXAMPLE 3

The following example demonstrates the use of an adenoviral vector prepared in accordance with the present invention to treat or prevent tumors in a host.

Radio-resistant human esophageal tumor cells derived from patient samples were injected into the right hind limb of nude mice in a single dose of $5\times10^6$ cells, and the mice were randomly divided into four treatment groups. Group 1 was treated only with a buffer solution, which was administered by direct injection into the tumor on day 0 and day 3. Group 2 received infrared radiation treatment consisting of 4 Gy doses of radiation administered on days 0, 1, 3 and 4 (for a total IR dose of 16 Gy). Group 3 was treated with the adenoviral vector of Example 1 (at $4\times10^8$ PU), which was administered by direct injection into the tumor on day 0 and day 3. Group 4 received the adenoviral vector treatment and the infrared radiation treatment.

Figure 2:
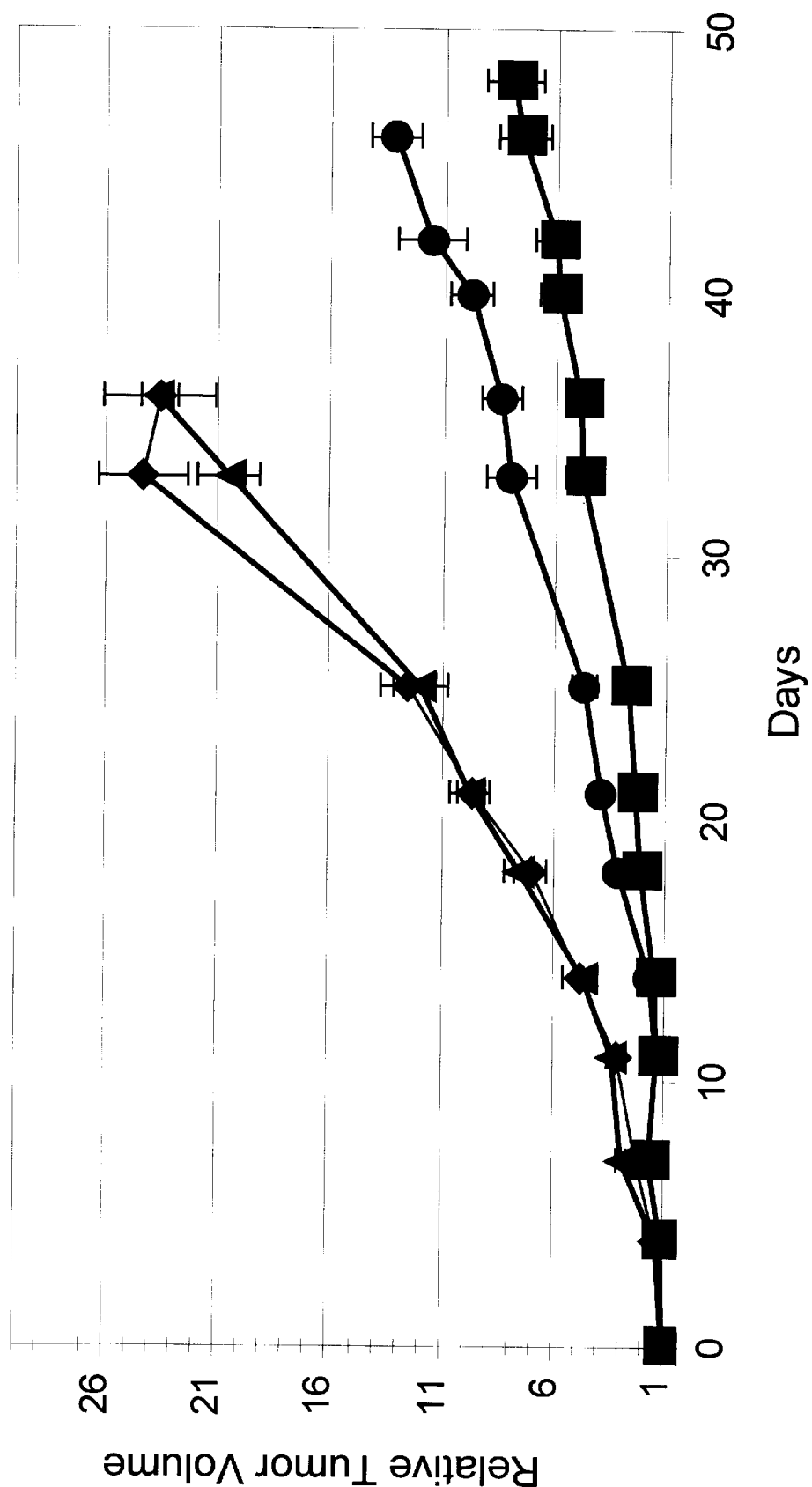
FIG. 2 is a plot of tumor volume against time for a tumor treated in a variety of manners, including with the adenoviral vector of the present invention.

Tumor volumes and animals weights were measured over 48 days. The tumor volumes were plotted against time to yield the tumor volume curves presented in FIG. 2, wherein the diamond-shaped data points (♦) represent data from group 1, the circular data points (●) represent data from group 2, triangular data points (▲) represent data from group 3, and the square data points (■) represent data from group 4. All animals remained healthy and no untoward effects were observed throughout the study. Animals from groups 1 and 2, however, were sacrificed at day 36 due to the large tumor burden (greater than 10% of body weight).

The tumor volume curves demonstrate substantially less tumor growth in animals treated with the vector and radiation (group 4) as compared to those treated with radiation alone (group 2) or the vector alone (group 3). This data demonstrates that the adenoviral vector of the present invention can be successfully used to treat a tumor in a host.

EXAMPLE 4

The following example demonstrates the use of an adenoviral vector prepared in accordance with the present invention to treat or prevent tumors in a host.

Radio-resistant esophageal tumor cells derived from patient samples were injected into the right hind limb of nude mice in a single dose of $5\times10^6$ cells, and the mice were randomly divided into four treatment groups. Group 1 was treated only with a buffer solution, which was administered by direct injection into the tumor on days 0, 3, 7 and 10. Group 2 received infrared radiation treatment consisting of 3 Gy doses of radiation administered on days 0, 1, 3, 4, 7, 8, 10 and 11 (for a total IR dose of 24 Gy). Group 3 was treated with the adenoviral vector of Example 1 (at $4\times10^8$ PU), which was administered by direct injection into the tumor on days 0, 3, 7 and 10. Group 4 received the adenoviral vector treatment and the infrared radiation treatment.

Figure 3:
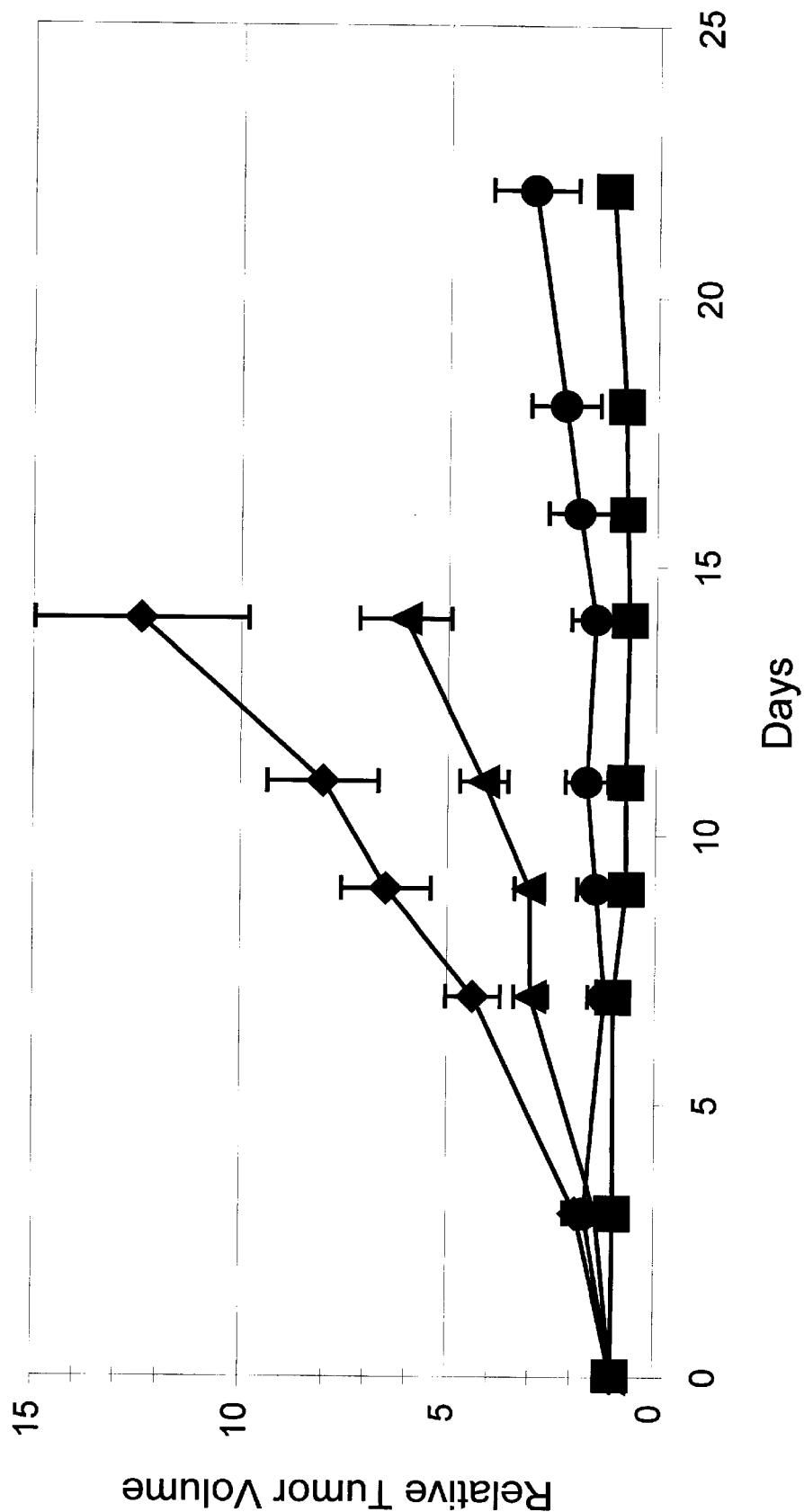
FIG. 3 is another plot of tumor volume against time for a tumor treated in a variety of manners, including with the adenoviral vector of the present invention.

Tumor volumes and animals weights were measured over 22 days. The tumor volumes were plotted against time to provide the tumor volume curves presented in FIG. 3, wherein the diamond-shaped data points (♦) represent data from group 1, the circular data points (●) represent data from group 2, triangular data points (▲) represent data from group 3, and the square data points (■) represent data from group 4. All animals remained healthy and no untoward effects were observed. Animals from groups 1 and 2, however, were sacrificed at day 15 due to the large tumor burden (greater than 10% of body weight).

The tumor volume curves demonstrate substantially less tumor growth in animals treated with the vector and radiation (group 4) as compared to those treated with radiation alone (group 2) or the vector alone (group 3). This data demonstrates that the adenoviral vector of the present invention can be successfully used to treat a tumor in a host.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. An adenoviral vector having the nucleic acid sequence of SEQ ID NO: 1.
2. A replication competent adenovirus-free stock of the adenoviral vector of claim 1.
3. A pharmaceutical composition comprising the adenoviral vector of claim 1 and a pharmaceutically acceptable carrier, wherein the pharmaceutical composition does not contain replication-competent adenoviruses.
4. A host cell comprising the adenoviral vector of claim 1.
5. A method of treating a tumor or cancer in a mammal comprising administering an anti-tumor or anti-cancer effective amount of the adenoviral vector of claim 1 directly to the tumor or cancer of the mammal.
6. The method of claim 5, further comprising the administration of radiation to the mammal.
7. The method of claim 6, wherein the adenoviral vector comprises a nucleic acid sequence coding for TNF, and wherein the radiation induces expression of the nucleic acid sequence coding for TNF to produce a therapeutic level of TNF in the mammal.
8. The method of claim 7, wherein the administration of radiation comprises the use of an internal source of radiation.
9. The method of claim 5, further comprising the administration of a TNF antagonist to the mammal.
10. The method of claim 9, wherein the TNF antagonist is at least one selected from the group comprising soluble TNF receptors and anti-TNF anti-bodies.
11. The method of claim 5, wherein an anti-tumor effective amount of the adenoviral vector is administered to a tumor in a mammal.
12. The method of claim 11, wherein the mammal is a human.
13. The method of claim 12, further comprising the administration of radiation to the human.
14. The method of claim 13, wherein the adenoviral vector comprises a nucleic acid sequence coding for TNF, and wherein the radiation induces expression of the nucleic acid sequence coding for TNF to produce a therapeutic level of TNF in the human.

15. The method of claim 14, wherein the administration of radiation comprises the use of an internal source of radiation.

16. The method of claim 12, further comprising the administration of a TNF antagonist to the human.

17. The method of claim 16, wherein the TNF antagonist is at least one selected from the group comprising soluble TNF receptors and anti-TNF anti-bodies.

* * * * *

SEQUENCE LISTING

```
<160> NUMBER OF SEQ ID NOS: 2

<210> SEQ ID NO 1
<211> LENGTH: 32798
<212> TYPE: DNA
<213> ORGANISM: Artificial Sequence
<220> FEATURE:
<223> OTHER INFORMATION: Synthetic construct

<400> SEQUENCE: 1
catcatcata atataccta ttttggattg aagccaatat gataatgagg gggtggagtt      60
tgtgacgtgg cgcggggcgt gggaacgggg cgggtgacgt agtagtgtgg cggaagtgtg     120
atgttgcaag tgtggcggaa cacatgtaag cgccggatgt ggtaaaagtg acgtttttgg    180
tgtgcgccgg tgtatacggg aagtgacaat tttcgcgcgg ttttaggcgg atgttgtagt    240
aaatttgggc gtaaccaagt aatatttggc cattttcgcg ggaaaactga ataagaggaa    300
gtgaaatctg aataattctg tgttactcat agcgcgtaat atttgtctag ggccgcgggg    360
actttgaccg tttacgtgga gactcgccca ggtgtttttc tcaggtgttt tccgcgttcc    420
gggtcaaagt tggcgtttta ttattatagt cagctctaga ctagatgcgc cgacccgaa    480 acgccatata aggagcagga aggatccccc gccggaacag accttatttg ggcagcgcct    540
tatatggagt ggcccaatat ggccctgccg cttccggctc tgggaggagg ggcgagcggg    600
ggttggggcg ggggcaagct gggaactcca ggcgcctggc ccgggaggcc actgctgctg    660
ttccaatact aggctttcca ggagcctgag cgctcgcgat gccggagcgg gtcgcagggt    720
ggaggtgccc accactcttg gatgggaggg cttcacgtca ctccgggtcc tcccggccgg    780
tccttccata ttagggcttc ctgcttccca tatatggcca tgtacgtcac ggcggaggcg    840
ggcccgtgct gttccagacc cttgaaatag aggccgattc ggggagtcgc gagagatccc    900
agcgcgcaga acttggggag ccgccgccgc gattcgccgc cgccgccagc ttccggtcga    960
ggaactgaaa aaccagaaag ttaactgggt aagtttagtc ttttttgtctt ttatttcagg   1020 tcccggatcc ggtggtggtg caaatcaaag aactgctcct cagtggatgt tgcctttact   1080
tctaggcctg tacggaagtg ttacttctgc tctaaaagct gcggaattgt acccgcggcc   1140
gcaaagggaa caaaagctgg gtaccgagct cgaatggggg gggggggggg gtactgaccc   1200
acggctccac cctctctccc ctggaaagga caccatgagc actgaaagca tgatccggga   1260
```

-continued

```
cgtggagctg gccgaggagg cgctccccaa gaagacaggg gggccccagg gctccaggcg    1320
gtgcttgttc ctcagcctct tctccttcct gatcgtggca ggcgccacca cgctcttctg    1380
cctgctgcac tttggagtga tcggccccca gagggaagag tccccagggg acctctctct    1440
aatcagccct ctggcccagg cagtcagatc atcttctcga accccgagtg acaagcctgt    1500
agcccatgtt gtagcaaacc ctcaagctga ggggcagctc cagtggctga accgccgggc    1560
caatgccctc ctggccaatg gcgtggagct gagagataac cagctggtgg tgccatcaga    1620
gggcctgtac ctcatctact cccaggtcct cttcaagggc caaggctgcc cctccaccca    1680
tgtgctcctc acccacacca tcagccgcat cgccgtctcc taccagacca aggtcaacct    1740
cctctctgcc atcaagagcc cctgccgagg ggagacccca gaggggctg aggccaagcc    1800
ctggtatgag cccatctatc tgggaggggt cttccagctg gagaagggtg accgactcag    1860
cgctgagatc aatcggcccg actatctcga ctttgccgag tctgggcagg tctactttgg    1920
gatcattgcc ctgtgaggag gacgaacatc caaccttccc aaacgcctcc cctgccccaa    1980
tccctttatt accccctcct tcagacaccc tcaacctctt ctggctcaaa agagaattg     2040
ggggcttagg gtcggaaccc aagcttgata tcgaattcct gcagcccggg ggatccacta    2100
gttctagagc ggccgcgggg atccagacat gataagatac attgatgagt ttggacaaac    2160
cacaactaga atgcagtgaa aaaaatgctt tatttgtgaa atttgtgatg ctattgcttt    2220
atttgtaacc attataagct gcaataaaca agttaacaac aacaattgca ttcattttat    2280
gtttcaggtt caggggggagg tgtgggaggt tttttcggat cctctagagt cgactagagt    2340
ggaaggtgct gaggtacgat gagacccgca ccaggtgcag accctgcgag tgtggcggta    2400
aacatattag gaaccagcct gtgatgctgg atgtgaccga ggagctgagg cccgatcact    2460
tggtgctggc ctgcacccgc gctgagtttg gctctagcga tgaagataca gattgaggta    2520
ctgaaatgtg tgggcgtggc ttaagggtgg gaaagaatat ataaggtggg ggtcttatgt    2580
agttttgtat ctgttttgca gcagccgccg ccgccatgag caccaactcg tttgatggaa    2640
gcattgtgag ctcatatttg acaacgcgca tgccccatg ggccggggtg cgtcagaatg    2700
tgatgggctc cagcattgat ggtcgccccg tcctgcccgc aaactctact accttgacct    2760
acgagaccgt gtctggaacg ccgttggaga ctgcagcctc cgccgccgct tcagccgctg    2820
cagccaccgc ccgcgggatt gtgactgact ttgctttcct gagcccgctt gcaagcagtg    2880
cagcttcccg ttcatccgcc cgcgatgaca agttgacggc tcttttggca caattggatt    2940
ctttgacccg ggaacttaat gtcgtttctc agcagctgtt ggatctgcgc cagcaggttt    3000
ctgccctgaa ggcttcctcc cctcccaatg cggtttaaaa cataaataaa aaaccagact    3060
ctgtttggat ttggatcaag caagtgtctt gctgtcttta tttaggggtt ttgcgcgcgc    3120
ggtaggcccg ggaccagcgg tctcggtcgt tgagggtcct gtgtattttt tccaggacgt    3180
ggtaaaggtg actctggatg ttcagataca tgggcataag cccgtctctg gggtggaggt    3240
agcaccactg cagagcttca tgctgcgggg tggtgttgta gatgatccag tcgtagcagg    3300
agcgctgggc gtggtgccta aaaatgtctt tcagtagcaa gctgattgcc aggggcaggc    3360
ccttggtgta agtgtttaca aagcggttaa gctgggatgg gtgcatacgt ggggatatga    3420
gatgcatctt ggactgtatt tttaggttgg ctatgttccc agccatatcc ctccggggat    3480
tcatgttgtg cagaaccacc agcacagtgt atccggtgca cttgggaaat ttgtcatgta    3540
gcttagaagg aaatgcgtgg aagaacttgg agacgccctt gtgacctcca agattttcca    3600
tgcattcgtc cataatgatg gcaatgggcc cacgggcggc ggcctgggcg aagatatttc    3660
```

-continued

```
tgggatcact aacgtcatag ttgtgttcca ggatgagatc gtcataggcc attttacaa    3720
agcgcgggcg gagggtgcca gactgcggta taatggttcc atccggccca ggggcgtagt   3780
taccctcaca gatttgcatt tcccacgctt tgagttcaga tgggggatc atgtctacct    3840
gcggggcgat gaagaaaacg gtttccgggg taggggagat cagctgggaa gaaagcaggt   3900
tcctgagcag ctgcgactta ccgcagccgg tgggcccgta aatcacacct attaccgggt   3960
gcaactggta gttaagagag ctgcagctgc cgtcatccct gagcagggg gccacttcgt    4020
taagcatgtc cctgactcgc atgttttccc tgaccaaatc cgccagaagg cgctcgccgc   4080
ccagcgatag cagttcttgc aaggaagcaa agttttcaa cggtttgaga ccgtccgccg    4140
taggcatgct tttgagcgtt tgaccaagca gttccaggcg gtcccacagc tcggtcacct   4200
gctctacggc atctcgatcc agcatatctc ctcgtttcgc gggttggggc ggctttcgct   4260
gtacggcagt agtcggtgct cgtccagacg ggccagggtc atgtctttcc acgggcgcag   4320
ggtcctcgtc agcgtagtct gggtcacggt gaagggtgc gctccgggct gcgcgctggc    4380
cagggtgcgc ttgaggctgg tcctgctggt gctgaagcgc tgccggtctt cgccctgcgc   4440
gtcggccagg tagcatttga ccatggtgtc atagtccagc ccctccgcgg cgtggccctt   4500
ggcgcgcagc ttgcccttgg aggaggcgcc gcacgagggg cagtgcagac ttttgagggc   4560
gtagagcttg ggcgcgagaa ataccgattc cggggagtag gcatccgcgc cgcaggcccc   4620
gcagacggtc tcgcattcca cgagccaggt gagctctggc cgttcgggt caaaaccag     4680
gtttccccca tgcttttga tgcgtttctt acctctggtt tccatgagcc ggtgtccacg    4740
ctcggtgacg aaaaggctgt ccgtgtcccc gtatacagac ttgagaggcc tgtcctcgag   4800
cggtgttccg cggtcctcct cgtatagaaa ctcggaccac tctgagacaa aggctcgcgt   4860
ccaggccagc acgaaggagg ctaagtggga ggggtagcgg tcgttgtcca ctaggggtc    4920
cactcgctcc agggtgtgaa gacacatgtc gccctcttcg gcatcaagga aggtgattgg   4980
tttgtaggtg taggccacgt gaccgggtgt tcctgaaggg gggctataaa aggggtggg    5040
ggcgcgttcg tcctcactct cttccgcatc gctgtctgcg agggccagct gttggggtga   5100
gtactccctc tgaaaagcgg gcatgacttc tgcgctaaga ttgtcagttt ccaaaaacga   5160
ggaggatttg atattcacct ggcccgcggt gatgcctttg agggtggccg catccatctg   5220
gtcagaaaag acaatctttt tgttgtcaag cttggtggca aacgacccgt agagggcgtt   5280
ggacagcaac ttggcgatgg agcgcaggt ttggtttttg tcgcgatcgg cgcgctcctt    5340
ggccgcgatg tttagctgca cgtattcgcg cgcaacgcac cgccattcgg gaaagacggt   5400
ggtgcgctcg tcgggcacca ggtgcacgcg ccaaccgcgg ttgtgcaggg tgacaaggtc   5460
aacgctggtg gctacctctc cgcgtaggcg ctcgttggtc cagcagaggc ggccgccctt   5520
gcgcgagcag aatggcggta gggggtctag ctgcgtctcg tccgggggt ctgcgtccac    5580
ggtaaagacc ccgggcagca ggcgcgcgtc gaagtagtct atcttgcatc cttgcaagtc   5640
tagcgcctgc tgccatgcgc gggcggcaag cgcgcgctcg tatgggttga gtgggggacc   5700
ccatggcatg gggtgggtga gcgcggaggc gtacatgccg caaatgtcgt aaacgtagag   5760
gggctctctg agtattccaa gatatgtagg gtagcatctt ccaccgcgga tgctggcgcg   5820
cacgtaatcg tatagttcgt gcgagggagc gaggaggtcg ggaccgaggt tgctacgggc   5880
gggctgctct gctcggaaga ctatctgcct gaagatggca tgtgagttgg atgatatggt   5940
tggacgctgg aagacgttga agctggcgtc tgtgagacct accgcgtcac gcacgaagga   6000
```

```
ggcgtaggag tcgcgcagct tgttgaccag ctcggcggtg acctgcacgt ctagggcgca   6060
gtagtccagg gtttccttga tgatgtcata cttatcctgt cccttttttt tccacagctc   6120
gcggttgagg acaaactctt cgcggtcttt ccagtactct tggatcggaa acccgtcggc   6180
ctccgaacgg taagagccta gcatgtagaa ctggttgacg gcctggtagg cgcagcatcc   6240
cttttctacg ggtagcgcgt atgcctgcgc ggccttccgg agcgaggtgt gggtgagcgc   6300
aaaggtgtcc ctgaccatga ctttgaggta ctggtatttg aagtcagtgt cgtcgcatcc   6360
gccctgctcc cagagcaaaa agtccgtgcg ctttttggaa cgcggatttg cagggcgaa    6420 ggtgacatcg ttgaagagta tctttcccgc gcgaggcata agttgcgtg tgatgcggaa    6480 gggtcccggc acctcggaac ggttgttaat tacctgggcg gcgagcacga tctcgtcaaa   6540
gccgttgatg ttgtggccca caatgtaaag ttccaagaag cgcgggatgc ccttgatgga   6600
aggcaatttt ttaagttcct cgtaggtgag ctcttcaggg gagctgagcc cgtgctctga   6660
aagggcccag tctgcaagat gagggttgga agcgacgaat gagctccaca ggtcacgggc   6720
cattagcatt tgcaggtggt cgcgaaaggt cctaaactgg cgacctatgg ccatttttc    6780 tggggtgatg cagtagaagg taagcgggtc ttgttcccag cggtcccatc caaggttcgc   6840
ggctaggtct cgcgcggcag tcactagagg ctcatctccg ccgaacttca tgaccagcat   6900
gaagggcacg agctgcttcc caaaggcccc catccaagta taggtctcta catcgtaggt   6960
gacaaagaga cgctcggtgc gaggatgcga gccgatcggg aagaactgga tctcccgcca   7020
ccaattggag gagtggctat tgatgtggtg aaagtagaag tccctgcgac gggccgaaca   7080
ctcgtgctgg cttttgtaaa aacgtgcgca gtactggcag cggtgcacgg gctgtacatc   7140
ctgcacgagg ttgacctgac gaccgcgcac aaggaagcag agtgggaatt tgagcccctc   7200
gcctggcggg tttggctggt ggtcttctac ttcggctgct tgtccttgac cgtctggctg   7260
ctcgagggga gttacggtgg atcggaccac cacgccgcgc gagcccaaag tccagatgtc   7320
cgcgcgcggc ggtcggagct tgatgacaac atcgcgcaga tgggagctgt ccatggtctg   7380
gagctcccgc ggcgtcaggt caggcggag ctcctgcagg tttacctcgc atagacgggt    7440
cagggcgcgg gctagatcca ggtgatacct aatttccagg ggctggttgg tggcggcgtc   7500
gatggcttgc aagaggccgc atccccgcgg cgcgactacg gtaccgcgcg gcgggcggtg   7560
ggccgcgggg gtgtccttgg atgatgcatc taaaagcggt gacgcgggcg agccccgga    7620 ggtagggggg gctccggacc cgccgggaga ggggcaggg gcacgtcggc gccgcgcgcg    7680
ggcaggagct ggtgctgcgc gcgtaggttg ctggcgaacg cgacgacgcg gcggttgatc   7740
tcctgaatct ggcgcctctg cgtgaagacg acgggcccgg tgagcttgag cctgaaagag   7800
agttcgacag aatcaatttc ggtgtcgttg acggcggcct ggcgcaaaat ctcctgcacg   7860
tctcctgagt tgtcttgata ggcgatctcg gccatgaact gctcgatctc ttcctcctgg   7920
agatctccgc gtccggctcg ctccacggtg gcggcgaggt cgttggaaat gcgggccatg   7980
agctgcgaga aggcgttgag gcctccctcg ttccagacgc ggctgtagac cacgcccct    8040 tcggcatcgc gggcgcgcat gaccacctgc gcgagattga gctccacgtg ccgggcgaag   8100
acggcgtagt ttcgcaggcg ctgaaagagg tagttgaggg tggtggcggt gtgttctgcc   8160
acgaagaagt acataaccca gcgtcgcaac gtggattcgt tgatatcccc caaggcctca   8220
aggcgctcca tggcctcgta gaagtccacg gcgaagttga aaaactggga gttgcgcgcc   8280
gacacggtta actcctcctc cagaagacgg atgagctcgg cgacagtgtc gcgcacctcg   8340
cgctcaaagg ctacaggggc ctcttcttct tcttcaatct cctcttccat aagggcctcc   8400
```

```
ccttcttctt cttctggcgg cggtggggga ggggggacac ggcggcgacg acggcgcacc   8460
gggaggcggt cgacaaagcg ctcgatcatc tccccgcggc gacggcgcat ggtctcggtg   8520
acggcgcggc cgttctcgcg ggggcgcagt tggaagacgc cgcccgtcat gtcccggtta   8580
tgggttggcg gggggctgcc atgcggcagg gatacggcgc taacgatgca tctcaacaat   8640
tgttgtgtag gtactccgcc gccgagggac ctgagcgagt ccgcatcgac cggatcggaa   8700
aacctctcga gaaaggcgtc taaccagtca cagtcgcaag gtaggctgag caccgtggcg   8760
ggcggcagcg ggcggcggtc ggggttgttt ctggcggagg tgctgctgat gatgtaatta   8820
aagtaggcgg tcttgagacg gcggatggtc gacagaagca ccatgtcctt gggtccggcc   8880
tgctgaatgc gcaggcggtc ggccatgccc caggcttcgt tttgacatcg gcgcaggtct   8940
ttgtagtagt cttgcatgag cctttctacc ggcacttctt cttctccttc ctcttgtcct   9000
gcatctcttg catctatcgc tgcggcggcg cggagtttg gccgtaggtg gcgccctctt    9060
cctcccatgc gtgtgacccc gaagcccctc atcggctgaa gcagggctag gtcggcgaca   9120
acgcgctcgc ctaatatggc ctgctgcacc tgcgtgaggg tagactggaa gtcatccatg   9180
tccacaaagc ggtggtatgc gcccgtgttg atggtgtaag tgcagttggc cataacggac   9240
cagttaacgg tctggtgacc cggctgcgag agctcggtgt acctgagacg cgagtaagcc   9300
ctcgagtcaa atacgtagtc gttgcaagtc cgcaccaggt actggtatcc caccaaaaag   9360
tgcggcggcg gctggcggta gagggccag cgtagggtgg ccggggctcc ggggcgaga    9420
tcttccaaca taaggcgatg atatccgtag atgtacctgg acatccaggt gatgccggcg   9480
gcggtggtgg aggcgcgcgg aaagtcgcgg acgcggttcc agatgttgcg cagcggcaaa   9540
aagtgctcca tggtcgggac gctctggccg gtcaggcgcg cgcaatcgtt gacgctctag   9600
ccgtgcaaaa ggagagcctg taagcgggca ctcttccgtg gtctggtgga taaattcgca   9660
agggtatcat ggcggacgac cggggttcga gccccgtatc cggccgtccg ccgtgatcca   9720
tgcggttacc gcccgcgtgt cgaacccagg tgtgcgacgt cagacaacgg gggagtgctc   9780
cttttggctt ccttccaggc gcggcggctg ctgcgctagc ttttttggcc actggccgcg   9840
cgcagcgtaa gcggttaggc tggaaagcga aagcattaag tggctcgctc cctgtagccg   9900
gagggttatt ttccaagggt tgagtcgcgg accccggt tcgagtctcg gaccggccgg     9960
actgcgcgcga acgggggttt gcctccccgt catgcaagac cccgcttgca aattcctccg  10020
gaaacaggga cgagccccctt ttttgctttt cccagatgca tccggtgctg cggcagatgc  10080
gcccccctcc tcagcagcgg caagagcaag agcagcggca gacatgcagg gcaccctccc   10140
ctcctcctac cgcgtcagga ggggcgacat ccgcggttga cgcggcagca gatggtgatt   10200
acgaacccccc gcggcgccgg gcccggcact acctggactt ggaggagggc gagggcctgg  10260
cgcggctagg agcgccctct cctgagcggt acccaagggt gcagctgaag cgtgatacgc   10320
gtgaggcgta cgtgccgcgg cagaacctgt ttcgcgaccg cgaggagag gagcccgagg    10380
agatgcggga tcgaaagttc cacgcagggc gcgagctgcg gcatggcctg aatcgcgagc   10440
ggttgctgcg cgaggaggac tttgagcccg acgcgcgaac cgggattagt cccgcgcgcg   10500
cacacgtggc ggccgccgac ctggtaaccg catacgagca gacggtgaac caggagatta   10560
actttcaaaa aagctttaac aaccacgtgc gtacgcttgt ggcgcgcgag gaggtggcta   10620
taggactgat gcatcgtgtgg gactttgtaa gcgcgctgga gcaaaaccca aatagcaagc   10680
cgctcatggc gcagctgttc cttatagtgc agcacagcag ggacaacgag gcattcaggg   10740
```

-continued

```
atgcgctgct aaacatagta gagcccgagg gccgctggct gctcgatttg ataaacatcc   10800
tgcagagcat agtggtgcag gagcgcagct tgagcctggc tgacaaggtg gccgccatca   10860
actattccat gcttagcctg ggcaagtttt acgcccgcaa gatataccat accccttacg   10920
ttcccataga caaggaggta aagatcgagg ggttctacat gcgcatggcg ctgaaggtgc   10980
ttaccttgag cgacgacctg ggcgtttatc gcaacgagcg catccacaag gccgtgagcg   11040
tgagccggcg gcgcgagctc agcgaccgcg agctgatgca cagcctgcaa agggccctgg   11100
ctggcacggg cagcggcgat agagaggcca agtcctactt tgacgcgggc gctgacctgc   11160
gctgggcccc aagccgacgc gccctggagg cagctggggc cggacctggg ctggcggtgg   11220 caccccgcgcg cgctggcaac gtcggcggcg tggaggaata tgacgaggac gatgagtacg   11280
agccagagga cggcgagtac taagcggtga tgtttctgat cagatgatgc aagacgcaac   11340
ggacccggcg gtgcgggcgg cgctgcagag ccagccgtcc ggccttaact ccacggacga   11400
ctggcgccag gtcatggacc gcatcatgtc gctgactgcg cgcaatcctg acgcgttccg   11460
gcagcagccg caggccaacc ggctctccgc aattctggaa gcggtggtcc cggcgcgcgc   11520
aaaccccacg cacgagaagg tgctggcgat cgtaaacgcg ctggccgaaa acagggccat   11580
ccggcccgac gaggccggcc tggtctacga cgcgctgctt cagcgcgtgg ctcgttacaa   11640
cagcggcaac gtgcagacca acctggaccg gctggtgggg gatgtgcgcg aggccgtggc   11700
gcagcgtgag cgcgcgcagc agcagggcaa cctgggctcc atggttgcac taaacgcctt   11760
cctgagtaca cagcccgcca acgtgccgcg gggacaggag gactcacca actttgtgag   11820 cgcactgcgg ctaatggtga ctgagacacc gcaaagtgag gtgtaccagt ctgggccaga   11880 ctatttttc cagaccagta gacaaggcct gcagaccgta aacctgagcc aggctttcaa   11940
aaacttgcag gggctgtggg gggtgcgggc tcccacaggc gaccgcgcga ccgtgtctag   12000
cttgctgacg cccaactcgc gcctgttgct gctgctaata gcgcccttca cggacagtgg   12060
cagcgtgtcc cgggacacat acctaggtca cttgctgaca ctgtaccgcg aggccatagg   12120
tcaggcgcat gtgacgagc atactttcca ggagattaca agtgtcagcc gcgcgctggg   12180
gcaggaggac acgggcagcc tggaggcaac cctaaactac ctgctgacca accggcggca   12240
gaagatcccc tcgttgcaca gtttaaacag cgaggaggag cgcattttgc gctacgtgca   12300
gcagagcgtg agccttaacc tgatgcgcga cggggtaacg cccagcgtgg cgctggacat   12360
gaccgcgcgc aacatggaac cgggcatgta tgcctcaaac cggccgttta tcaaccgcct   12420
aatggactac ttgcatcgcg cggccgccgt gaaccccgag tatttcacca atgccatctt   12480
gaacccgcac tggctaccgc cccctggttt ctacaccggg ggattcgagg tgcccgaggg   12540
taacgatgga ttcctctggg acgacataga cgacagcgtg ttttccccgc aaccgcagac   12600
cctgctagag ttgcaacagc gcgagcaggc agaggcggcg ctgcgaaagg aaagcttccg   12660
caggccaagc agcttgtccg atctaggcgc tgcggccccg cggtcagatg ctagtagccc   12720
atttccaagc ttgataggt ctcttaccag cactcgcacc acccgcccgc gcctgctggg   12780
cgaggaggag tacctaaaca actcgctgct gcagccgcag cgcgaaaaaa acctgcctcc   12840
ggcatttccc aacaacggga tagagagcct agtggacaag atgagtagat ggaagacgta   12900
cgcgcaggag cacaggcacg tgccaggccc gcgcccgccc accgtcgtc aaaggcacga   12960 ccgtcagcgg ggtctggtgt gggaggacga tgactcggca gacgcagca gcgtcctgga   13020 tttgggaggg agtggcaacc cgtttgcgca ccttcgcccc aggctgggga gaatgttta   13080 aaaaaaaaaa agcatgatgc aaaataaaaa actcaccaag gccatggcac cgagcgttgg   13140
```

```
ttttcttgta ttcccottag tatgcggcgc gcggcgatgt atgaggaagg tcctcctccc   13200
tcctacgaga gtgtggtgag cgcggcgcca gtggcggcgg cgctgggttc tcccttcgat   13260
gctcccctgg acccgccgtt tgtgcctccg cggtacctgc ggcctaccgg ggggagaaac   13320
agcatccgtt actctgagtt ggcacccta ttcgacacca cccgtgtgta cctggtggac   13380
aacaagtcaa cggatgtggc atccctgaac taccagaacg accacagcaa ctttctgacc   13440
acggtcattc aaaacaatga ctacagcccg ggggaggcaa gcacacagac catcaatctt   13500
gacgaccggt cgcactgggg cggcgacctg aaaaccatcc tgcataccaa catgccaaat   13560
gtgaacgagt tcatgtttac caataagttt aaggcgcggg tgatggtgtc gcgcttgcct   13620
actaaggaca atcaggtgga gctgaaatac gagtgggtgg agttcacgct gcccgagggc   13680
aactactccg agaccatgac catagacctt atgaacaacg cgatcgtgga gcactacttg   13740
aaagtgggca gacagaacgg ggttctggaa agcgacatcg gggtaaagtt tgacacccgc   13800
aacttcagac tggggtttga ccccgtcact ggtcttgtca tgcctggggt atatacaaac   13860
gaagccttcc atccagacat cattttgctg ccaggatgcg gggtggactt cacccacagc   13920
cgcctgagca acttgttggg catccgcaag cggcaaccct tccaggaggg ctttaggatc   13980
acctacgatg atctggaggg tggtaacatt cccgcactgt tggatgtgga cgcctaccag   14040
gcgagcttga aagatgacac cgaacagggc gggggtggcg caggcggcag caacagcagt   14100
ggcagcggcg cggaagagaa ctccaacgcg gcagccgcgg caatgcagcc ggtggaggac   14160
atgaacgatc atgccattcg cggcgacacc tttgccacac gggctgagga aagcgcgct   14220 gaggccgaag cagcggccga agctgccgcc cccgctgcgc aacccgaggt cgagaagcct   14280
cagaagaaac cggtgatcaa acccctgaca gaggacagca agaaacgcag ttacaaccta   14340
ataagcaatg acagcacctt cacccagtac cgcagctggt accttgcata caactacggc   14400
gaccctcaga ccggaatccg ctcatggacc ctgctttgca ctcctgacgt aacctgcggc   14460
tcggagcagg tctactggtc gttgccagac atgatgcaag accccgtgac cttccgctcc   14520
acgcgccaga tcagcaactt tccggtggtg ggcgccgagc tgttgcccgt gcactccaag   14580
agcttctaca cgaccaggc cgtctactcc caactcatcc gccagtttac ctctctgacc   14640
cacgtgttca atcgctttcc cgagaaccag attttggcgc cccgccagc ccccaccatc   14700 accaccgtca gtgaaaacgt tcctgctctc acagatcacg ggacgctacc gctgcgcaac   14760
agcatcggag gagtccagcg agtgaccatt actgacgcca gacgccgcac ctgccctac   14820 gtttacaagg ccctgggcat agtctcgccg cgcgtcctat cgagccgcac ttttgagca   14880 agcatgtcca tccttatatc gcccagcaat aacacaggct ggggcctgcg cttcccaagc   14940
aagatgtttg gcggggccaa gaagcgctcc gaccaacacc cagtgcgcgt gcgcgggcac   15000
taccgcgcgc cctgggcgc gcacaaacgc ggccgcactg ggcgcaccac cgtcgatgac   15060
gccatcgacg cggtggtgga ggaggcgcgc aactacacgc ccacgccgcc accagtgtcc   15120
acagtggacg cggccattca gaccgtggtg cgcggagccc ggcgctatgc taaaatgaag   15180
agacggcgga ggcgcgtagc acgtcgccac cgccgccgac ccggcactgc gcccaacgc   15240 gcggcggcgc ccctgcttaa ccgcgcacgt cgcaccggcc gacgggcggc catgcgggcc   15300
gctcgaaggc tggccgcggg tattgtcact gtgccccca ggtccaggcg acgagcggcc   15360
gccgcagcag ccgcggccat tagtgctatg actcagggtc gcaggggcaa cgtgtattgg   15420
gtgcgcgact cggttagcgg cctgcgcgtg cccgtgcgca cccgccccc gcgcaactag   15480
```

```
attgcaagaa aaaactactt agactcgtac tgttgtatgt atccagcggc ggcggcgcgc   15540
aacgaagcta tgtccaagcg caaaatcaaa gaagagatgc tccaggtcat cgcgccggag   15600
atctatggcc ccccgaagaa ggaagagcag gattacaagc cccgaaagct aaagcgggtc   15660
aaaaagaaaa agaaagatga tgatgatgaa cttgacgacg aggtggaact gctgcacgct   15720
accgcgccca ggcgacgggt acagtggaaa ggtcgacgcg taaaacgtgt tttgcgaccc   15780
ggcaccaccg tagtctttac gcccggtgag cgctccaccc gcacctacaa gcgcgtgtat   15840
gatgaggtgt acggcgacga ggacctgctt gagcaggcca acgagcgcct cggggagttt   15900
gcctacggaa agcggcataa ggacatgctg gcgttgccgc tggacgaggg caacccaaca   15960
cctagcctaa agcccgtaac actgcagcag gtgctgcccg cgcttgcacc gtccgaagaa   16020
aagcgcggcc taaagcgcga gtctggtgac ttggcaccca ccgtgcagct gatggtaccc   16080
aagcgccagc gactgaaaga tgtcttggaa aaaatgaccg tggaacctgg gctggagccc   16140
gaggtccgcg tgcggccaat caagcaggtg gcgccgggac tgggcgtgca gaccgtggac   16200
gttcagatac ccactaccag tagcaccagt attgccaccg ccacagaggg catggagaca   16260
caaacgtccc cggttgcctc agcggtggcg gatgccgcgg tgcaggcggt cgctgcggcc   16320
gcgtccaaga cctctacgga ggtgcaaacg gaccgtggga tgtttcgcgt ttcagccccc   16380
cggcgcccgc gcggttcgag gaagtacggc gccgccagcc gctactgcc cgaatatgcc   16440 ctacatcctt ccattgcgcc taccccggc tatcgtggct acacctaccg ccccagaaga   16500
cgagcaacta cccgacgccg aaccaccact ggaacccgcc gccgccgtcg ccgtcgccag   16560
cccgtgctgg ccccgatttc cgtgcgcagg gtggctcgcg aaggaggcag gaccctggtg   16620
ctgccaacag cgcgctacca ccccagcatc gtttaaaagc cggtctttgt ggttcttgca   16680
gatatggccc tcacctgccg cctccgtttc ccggtgccgg gattccgagg aagaatgcac   16740
cgtaggaggg gcatggccgg ccacggcctg acgggcggca tgcgtcgtgc gcaccaccgg   16800
cggcggcgcg cgtcgcaccg tcgcatgcgc ggcggtatcc tgcccctcct tattccactg   16860
atcgccgcgg cgattggcgc cgtgcccgga attgcatccg tggccttgca ggcgcagaga   16920
cactgattaa aaacaagttg catgtggaaa aatcaaaata aaagtctgg actctcacgc   16980 tcgcttggtc ctgtaactat tttgtagaat ggaagacatc aactttgcgt ctctggcccc   17040
gcgacacggc tcgcgcccgt tcatgggaaa ctggcaagat atcggcacca gcaatatgag   17100
cggtggcgcc ttcagctggg gctcgctgtg gagcggcatt aaaaatttcg gttccaccgt   17160
taagaactat ggcagcaagg cctggaacag cagcacaggc cagatgctga gggataagtt   17220
gaaagagcaa aatttccaac aaaaggtggt agatggcctg gcctctggca ttagcggggt   17280
ggtggacctg gccaaccagg cagtgcaaaa taagattaac agtaagcttg atccccgccc   17340
tcccgtagag gagcctccac cggccgtgga gacagtgtct ccagaggggc gtggcgaaaa   17400
gcgtccgcgc cccgacaggg aagaaactct ggtgacgcaa atagacgagc tccctcgta   17460 cgaggaggca ctaaagcaag gcctgccac acccgtccc atcgcgccca tggctaccgg   17520
agtgctgggc cagcacacac ccgtaacgct ggacctgcct cccccgccg acacccagca   17580 gaaacctgtg ctgccaggcc cgaccgccgt tgttgtaacc cgtcctagcc gcgcgtccct   17640
gcgccgcgcc gccagcggtc cgcgatcgtt gcggcccgta ccagtggca actggcaaag   17700 cacactgaac agcatcgtgg gtctgggggt gcaatccctg aagcgccgac gatgcttctg   17760
aatagctaac gtgtcgtatg tgtgtcatgt atgcgtccat gtcgccgcca gaggagctgc   17820
tgagccgccg cgcgcccgct ttccaagatg gctacccctt cgatgatgcc gcagtggtct   17880
```

-continued

```
tacatgcaca tctcgggcca ggacgcctcg gagtacctga gccccgggct ggtgcagttt    17940
gcccgcgcca ccgagacgta cttcagcctg aataacaagt ttagaaaccc cacggtggcg    18000
cctacgcacg acgtgaccac agaccggtcc cagcgtttga cgctgcggtt catccctgtg    18060
gaccgtgagg atactgcgta ctcgtacaag gcgcggttca ccctagctgt gggtgataac    18120
cgtgtgctgg acatggcttc cacgtacttt gacatccgcg gcgtgctgga caggggccct    18180
acttttaagc cctactctgg cactgcctac aacgccctgg ctcccaaggg tgccccaaat    18240
ccttgcgaat gggatgaagc tgctactgct cttgaaataa acctagaaga agaggacgat    18300
gacaacgaag acgaagtaga cgagcaagct gagcagcaaa aaactcacgt atttgggcag    18360
gcgccttatt ctggtataaa tattacaaag gagggtattc aaataggtgt cgaaggtcaa    18420
acacctaaat atgccgataa acatttcaa cctgaacctc aaataggaga atctcagtgg    18480
tacgaaactg aaattaatca tgcagctggg agagtcctta aaaagactac cccaatgaaa    18540
ccatgttacg gttcatatgc aaaacccaca aatgaaaatg gagggcaagg cattcttgta    18600
aagcaacaaa atgaaaagct agaaagtcaa gtggaaatgc aattttctc aactactgag    18660 gcgaccgcag gcaatggtga taacttgact cctaaagtgg tattgtacag tgaagatgta    18720
gatatagaaa ccccagacac tcatatttct tacatgccca ctattaagga aggtaactca    18780
cgagaactaa tgggccaaca atctatgccc aacaggccta attacattgc ttttagggac    18840 aatttttattg gtctaatgta ttacaacagc acgggtaata tgggtgttct ggcgggccaa    18900
gcatcgcagt tgaatgctgt tgtagatttg caagacagaa acacagagct ttcataccag    18960
cttttgcttg attccattgg tgatagaacc aggtactttt ctatgtggaa tcaggctgtt    19020
gacagctatg atccagatgt tagaattatt gaaaatcatg gaactgaaga tgaacttcca    19080
aattactgct ttccactggg aagtgtgatt aatacagaga ctcttaccaa ggtaaaacct    19140
aaaacaggtc aggaaaatgg atgggaaaaa gatgctacag aattttcaga taaaaatgaa    19200
ataagagttg gaaataattt tgccatggaa atcaatctaa atgccaacct gtggagaaat    19260
ttcctgtact ccaacatagc gctgtatttg cccgacaagc taaagtacag tccttccaac    19320
gtaaaaattt ctgataaccc aaacacctac gactacatga acaagcgagt ggtggctccc    19380
gggttagtgg actgctacat taaccttgga gcacgctggt cccttgacta tatggacaac    19440
gtcaacccat ttaaccacca ccgcaatgct ggcctgcgct accgctcaat gttgctgggc    19500
aatggtcgct atgtgccctt ccacatccag gtgcctcaga agttctttgc cattaaaaac    19560
ctccttctcc tgccgggctc atacacctac gagtggaact tcaggaagga tgttaacatg    19620
gttctgcaga gctccctagg aaatgaccta agggttgacg gagccagcat taagtttgat    19680
agcatttgcc tttacgccac cttcttcccc atggcccaca acaccgcctc cacgcttgag    19740
gccatgctta gaaacgacac caacgaccag tcctttaacg actatctctc cgccgccaac    19800
atgctctacc ctatcccgc caacgctacc aacgtgccca tatccatccc ctcccgcaac    19860
tgggcggctt ccgcggctg ggccttcacg cgccttaaga ctaaggaaac cccatcactg    19920
ggctcgggct acgacccta ttacacctac tctggctcta taccctacct agatggaacc    19980
ttttacctca ccacaccctt taagaaggtg ccattacct ttgactcttc tgtcagctgg    20040
cctggcaatg accgcctgct tacccccaac gagtttgaaa ttaagcgctc agttgacggg    20100
gagggttaca acgttgccca gtgtaacatg accaaagact ggttcctggt acaaatgcta    20160
gctaactaca acattggcta ccagggcttc tatatcccag agagctacaa ggaccgcatg    20220
```

| | |
|---|---|
| tactccttct ttagaaactt ccagcccatg agccgtcagg tggtggatga tactaaatac | 20280 |
| aaggactacc aacaggtggg catcctacac caacacaaca actctggatt tgttggctac | 20340 |
| cttgccccca ccatgcgcga aggacaggcc taccctgcta acttccccta tccgcttata | 20400 |
| ggcaagaccg cagttgacag cattacccag aaaaagtttc tttgcgatcg cacccttggg | 20460 |
| cgcatcccat tctccagtaa ctttatgtcc atgggcgcac tcacagacct gggccaaaac | 20520 |
| cttctctacg ccaactccgc ccacgcgcta gacatgactt tgaggtgga tcccatggac | 20580 |
| gagcccaccc ttctttatgt tttgtttgaa gtctttgacg tggtccgtgt gcaccggccg | 20640 |
| caccgcggcg tcatcgaaac cgtgtacctg cgcacgccct tctcggccgg caacgccaca | 20700 |
| acataaagaa gcaagcaaca tcaacaacag ctgccgccat gggctccagt gagcaggaac | 20760 |
| tgaaagccat tgtcaaagat cttggttgtg ggccatattt tttgggcacc tatgacaagc | 20820 |
| gctttccagg ctttgtttct ccacacaagc tcgcctgcgc catagtcaat acggccggtc | 20880 |
| gcgagactgg gggcgtacac tggatggcct ttgcctggaa cccgcactca aaaacatgct | 20940 |
| acctctttga gccctttggc ttttctgacc agcgactcaa gcaggtttac cagtttgagt | 21000 |
| acgagtcact cctgcgccgt agcgccattg cttcttcccc cgaccgctgt ataacgctgg | 21060 |
| aaaagtccac ccaaagcgta caggggccca actcggccgc ctgtggacta ttctgctgca | 21120 |
| tgtttctcca cgcctttgcc aactggcccc aaactcccat ggatcacaac cccaccatga | 21180 |
| accttattac cggggtaccc aactccatgc tcaacagtcc ccaggtacag cccaccctgc | 21240 |
| gtcgcaacca ggaacagctc tacagcttcc tggagcgcca ctcgccctac ttccgcagcc | 21300 |
| acagtgcgca gattaggagc gccacttctt tttgtcactt gaaaaacatg taaaaataat | 21360 |
| gtactagaga cactttcaat aaaggcaaat gcttttattt gtacactctc gggtgattat | 21420 |
| ttacccccac ccttgccgtc tgcgccgttt aaaaatcaaa ggggttctgc cgcgcatcgc | 21480 |
| tatgcgccac tggcagggac acgttgcgat actggtgttt agtgctccac ttaaactcag | 21540 |
| gcacaaccat ccgcggcagc tcggtgaagt tttcactcca caggctgcgc accatcacca | 21600 |
| acgcgtttag caggtcgggc gccgatatct tgaagtcgca gttggggcct ccgccctgcg | 21660 |
| cgcgcgagtt gcgatacaca gggttgcagc actggaacac tatcagcgcc gggtggtgca | 21720 |
| cgctggccag cacgctcttg tcggagatca gatccgcgtc caggtcctcc gcgttgctca | 21780 |
| gggcgaacgg agtcaacttt ggtagctgcc ttcccaaaaa gggcgcgtgc ccaggctttg | 21840 |
| agttgcactc gcaccgtagt ggcatcaaaa ggtgaccgtg cccggtctgg gcgttaggat | 21900 |
| acagcgcctg cataaaagcc ttgatctgct taaaagccac ctgagccttt gcgccttcag | 21960 |
| agaagaacat gccgcaagac ttgccggaaa actgattggc cggacaggcc gcgtcgtgca | 22020 |
| cgcagcacct tgcgtcggtg ttggagatct gcaccacatt tcggcccac cggttcttca | 22080 |
| cgatcttggc cttgctagac tgctccttca gcgcgcgctg cccgttttcg ctcgtcacat | 22140 |
| ccatttcaat cacgtgctcc ttatttatca taatgcttcc gtgtagacac ttaagctcgc | 22200 |
| cttcgatctc agcgcagcgg tgcagccaca acgcgcagcc cgtgggctcg tgatgcttgt | 22260 |
| aggtcacctc tgcaaacgac tgcaggtacg cctgcaggaa tcgccccatc atcgtcacaa | 22320 |
| aggtcttgtt gctggtgaag gtcagctgca acccgcggtg ctcctcgttc agccaggtct | 22380 |
| tgcatacggc cgccagagct tccacttggt caggcagtag tttgaagttc gcctttagat | 22440 |
| cgttatccac gtggtacttg tccatcagcg cgcgcgcagc ctccatgccc ttctcccacg | 22500 |
| cagacacgat cggcacactc agcgggttca tcaccgtaat ttcactttcc gcttcgctgg | 22560 |
| gctcttcctc ttcctcttgc gtccgcatac cacgcgccac tgggtcgtct tcattcagcc | 22620 |

```
gccgcactgt gcgcttacct cctttgccat gcttgattag caccggtgggg ttgctgaaac    22680 ccaccatttg tagcgccaca tcttctcttt cttcctcgct gtccacgatt acctctggtg    22740
atggcgggcg ctcgggcttg ggagaagggc gcttcttttt cttcttgggc gcaatggcca    22800
aatccgccgc cgaggtcgat ggccgcgggc tgggtgtgcg cggcaccagc gcgtcttgtg    22860
atgagtcttc ctcgtcctcg gactcgatac gccgcctcat ccgctttttt gggggcgccc    22920
ggggaggcgg cggcgacggg gacggggacg acacgtcctc catggttggg ggacgtcgcg    22980
ccgcaccgcg tccgcgctcg ggggtggttt cgcgctgctc ctcttcccga ctggccattt    23040
ccttctccta taggcagaaa aagatcatgg agtcagtcga gaagaaggac agcctaaccg    23100 cccccctctga gttcgccacc accgcctcca ccgatgccgc caacgcgcct accaccttcc    23160
ccgtcgaggc accccccgctt gaggaggagg aagtgattat cgagcaggac ccaggttttg    23220
taagcgaaga cgacgaggac cgctcagtac aacagagga taaaaagcaa gaccaggaca    23280
acgcagaggc aaacgaggaa caagtcgggc ggggggacga aaggcatggc gactacctag    23340
atgtgggaga cgacgtgctg ttgaagcatc tgcagcgcca gtgcgccatt atctgcgacg    23400
cgttgcaaga gcgcagcgat gtgcccctcg ccatagcgga tgtcagcctt gcctacgaac    23460
gccacctatt ctcaccgcgc gtaccccccca acgccaaga aaacggcaca tgcgagccca    23520
acccgcgcct caacttctac cccgtatttg ccgtgccaga ggtgcttgcc acctatcaca    23580 tcttttttcca aaactgcaag ataccccctat cctgccgtgc caaccgcagc cgagcggaca    23640
agcagctggc cttgcggcag ggcgctgtca tacctgatat cgcctcgctc aacgaagtgc    23700
caaaaatctt tgagggtctt ggacgcgacg agaagcgcgc ggcaaacgct ctgcaacagg    23760
aaaacagcga aaatgaaagt cactctggag tgttggtgga actcgagggt gacaacgcgc    23820
gcctagccgt actaaaacgc agcatcgagg tcacccactt tgcctacccg gcacttaacc    23880
taccccccaa ggtcatgagc acagtcatga gtgagctgat cgtgcgccgt gcgcagcccc    23940
tggagaggga tgcaaatttg caagaacaaa cagaggaggg cctacccgca gttggcgacg    24000
agcagctagc gcgctggctt caaacgcgcg agcctgccga cttggaggag cgacgcaaac    24060
taatgatggc cgcagtgctc gttaccgtgg agcttgagtg catgcagcgg ttctttgctg    24120
acccggagat gcagcgcaag ctagaggaaa cattgcacta cacctttcga cagggctacg    24180
tacgccaggc ctgcaagatc tccaacgtgg agctctgcaa cctggtctcc taccttggaa    24240
ttttgcacga aaaccgcctt gggcaaaacg tgcttcattc cacgctcaag ggcgaggcgc    24300
gccgcgacta cgtccgcgac tgcgtttact tatttctatg ctacacctgg cagacggcca    24360
tgggcgtttg gcagcagtgc ttggaggagt gcaacctcaa ggagctgcag aaactgctaa    24420
agcaaaactt gaaggaccta tggacggcct tcaacgagcg ctccgtggcc gcgcacctgg    24480
cggacatcat tttcccccgaa cgcctgctta aaaccctgca acagggtctg ccagacttca    24540
ccagtcaaag catgttgcag aactttagga actttatcct agagcgctca ggaatcttgc    24600
ccgccacctg ctgtgcactt cctagcgact tgtgcccat taagtaccgc gaatgccctc    24660
cgccgctttg ggccactgc taccttctgc agctagccaa ctaccttgcc taccactctg    24720
acataatgga agacgtgagc ggtgacggtc tactggagtg tcactgtcgc tgcaacctat    24780
gcaccccgca ccgctccctg gtttgcaatt cgcagctgct taacgaaagt caaattatcg    24840 gtaccttttga gctgcagggt ccctcgcctg acgaaaagtc cgcggctccg gggttgaaac    24900
tcactccggg gctgtggacg tcggcttacc ttcgcaaatt tgtacctgag gactaccacg    24960
```

-continued

```
cccacgagat taggttctac gaagaccaat cccgcccgcc aaatgcggag cttaccgcct   25020
gcgtcattac ccagggccac attcttggcc aattgcaagc catcaacaaa gcccgccaag   25080
agtttctgct acgaaaggga cgggggtttt acttggaccc ccagtccggc gaggagctca   25140
acccaatccc cccgccgccg cagccctatc agcagcagcc gcgggcccct tgcttccagg   25200
atggcaccca aaaagaagct gcagctgccg ccgccaccca cggacgagga ggaatactgg   25260
gacagtcagg cagaggaggt tttggacgag gaggaggagg acatgatgga agactgggag   25320
agcctagacg aggaagcttc cgaggtcgaa gaggtgtcag acgaaacacc gtcaccctcg   25380
gtcgcattcc cctcgccggc gccccagaaa tcggcaaccg gttccagcat ggctacaacc   25440
tccgctcctc aggcgccgcc ggcactgccc gttcgccgac ccaaccgtag atgggacacc   25500
actggaacca gggccggtaa gtccaagcag ccgccgccgt tagcccaaga gcaacaacag   25560
cgccaaggct accgctcatg gcgcgggcac aagaacgcca tagttgcttg cttgcaagac   25620
tgtgggggca acatctcctt cgcccgccgc tttcttctct accatcacgg cgtggccttc   25680
ccccgtaaca tcctgcatta ctaccgtcat ctctacagcc catactgcac cggcggcagc   25740
ggcagcggca gcaacagcag cggccacaca gaagcaaagg cgaccggata gcaagactct   25800
gacaaagccc aagaaatcca cagcggcgga agcagcagga ggaggagcgc tgcgtctggc   25860
gcccaacgaa cccgtatcga cccgcgagct tagaaacagg attttttccca ctctgtatgc   25920
tatatttcaa cagagcaggg gccaagaaca agagctgaaa ataaaaaaca ggtctctgcg   25980
atccctcacc cgcagctgcc tgtatcacaa aagcgaagat cagcttcggc gcacgctgga   26040
agacgcggag gctctcttca gtaaatactg cgcgctgact cttaaggact agtttcgcgc   26100
cctttctcaa atttaagcgc gaaaactacg tcatctccag cggccacacc cggcgccagc   26160
acctgtcgtc agcgccatta tgagcaagga aattcccacg ccctacatgt ggagttacca   26220
gccacaaatg ggacttgcgg ctggagctgc ccaagactac tcaacccgaa taaactacat   26280
gagcgcggga ccccacatga tatcccgggt caacggaatc cgcgcccacc gaaaccgaat   26340
tctcttggaa caggcggcta ttaccaccac acctcgtaat aaccttaatc cccgtagttg   26400
gcccgctgcc ctggtgtacc aggaaagtcc cgctcccacc actgtggtac ttcccagaga   26460
cgccaggcc gaagttcaga tgactaactc aggggcgcag cttgcgggcg ctttcgtca   26520
cagggtgcgg tcgcccgggc agggtataac tcacctgaca atcagagggc gaggtattca   26580
gctcaacgac gagtcggtga gctcctcgct tggtctccgt ccggacggga catttcgat   26640
cggcggcgcc ggccgctctt cattcacgcc tcgtcaggca atcctaactc tgcagacctc   26700
gtcctctgag ccgcgctctg gaggcattgg aactctgcaa tttattgagg agtttgtgcc   26760
atcggtctac tttaaccccct tctcgggacc tcccggccac tatccggatc aatttattcc   26820
taactttgac gcggtaaagg actcggcgga cggctacgac tgaatgttaa gtggagaggc   26880
agagcaactg cgcctgaaac acctggtcca ctgtcgccgc cacaagtgct tgcccgcga   26940
ctccggtgag ttttgctact ttgaattgcc cgaggatcat atcgagggcc cggcgcacgg   27000
cgtccggctt accgcccagg gagagcttgc ccgtagcctg attcgggagt ttacccagcg   27060
cccccctgcta gttgagcggg acaggggacc ctgtgttctc actgtgattt gcaactgtcc   27120
taaccctgga ttacatcaag atctttgttg ccatctctgt gctgagtata ataaatacag   27180
aaattaaaat atactggggc tcctatcgcc atcctgtaaa cgccaccgtc ttcacccgcc   27240
caagcaaacc aaggcgaacc ttacctggta ctttttaacat ctctccctct gtgatttaca   27300
acagtttcaa cccagacgga gtgagtctac gagagaacct ctccgagctc agctactcca   27360
```

```
tcagaaaaaa caccaccctc cttacctgcc gggaacgtac gagtgcgtca ccggccgctg     27420
caccacacct accgcctgac cgtaaaccag acttttccg  acagacctc  ataactctg     27480 tttaccagaa caggaggtga gcttagaaaa cccttagggt attaggccaa aggcgcagct     27540 actgtgggt  ttatgaacaa ttcaagcaac tctacgggct attctaattc aggtttctct     27600
agaaatggac ggaattatta cagagcagcg cctgctagaa agacgcaggg cagcggccga     27660
gcaacagcgc atgaatcaag agctccaaga catggttaac ttgcaccagt gcaaaggggg     27720
tatcttttgt ctggtaaagc aggccaaagt cacctacgca agtaatacca ccggacaccg     27780
ccttagctac aagttgccaa ccaagcgtca gaaattggtg gtcatggtgg gagaaaagcc     27840
cattaccata actcagcact cggtagaaac cgaaggctgc attcactcac cttgtcaagg     27900
acctgaggat ctctgcaccc ttattaagac cctgtgcggt ctcaaagatc ttattccctt     27960
taactaataa aaaaaaataa taagcatcca cttacttaaa atcagttagc aaatttctgt     28020
ccagtttatt cagcagcacc tccttgccct cctcccagct ctggtattgc agcttcctcc     28080
tggctgcaaa ctttctccac aatctaaatg gaatgtcagt ttcctcctgt tcctgtccat     28140
ccgcacccac tatcttcatg ttgttgcaga tgaagcgcgc aagaccgtct gaagatacct     28200 tcaacccgt  gtatccatat gacacggaaa ccggtcctcc aactgtgcct tttcttactc     28260 ctcccttgt  atccccaat  gggtttcaag agagtccccc tggggtactc tctttgcgcc     28320
tatccgaacc tctagttacc tccaatggca tgcttgcgct caaatgggc  aacgcctct      28380 ctctggacga ggccggcaac cttacctccc aaaatgtaac cactgtgagc ccacctctca     28440
aaaaaaccaa gtcaaacata aacctggaaa tatctgcacc cctcacagtt acctcagaag     28500
ccctaactgt ggctgccgcc gcacctctaa tggtcgcggg caacacactc accatgcaat     28560
cacaggcccc gctaaccgtg cacgactcca aacttagcat tgccacccaa ggaccccta     28620 cagtgtcaga aggaaagcta gccctgcaaa catcaggccc cctcaccacc accgatagca     28680
gtacccttac tatcactgcc tcacccctc  taactactgc cactggtagc ttgggcattg     28740
acttgaaaga gcccatttat acacaaaatg gaaaactagg actaaagtac ggggctcctt     28800
tgcatgtaac agacgaccta aacactttga ccgtagcaac tggtccaggt gtgactatta     28860
ataatacttc cttgcaaact aaagttactg gagccttggg ttttgattca caaggcaata     28920
tgcaacttaa tgtagcagga ggactaagga ttgattctca aaacagacgc cttatacttg     28980
atgttagtta tccgtttgat gctcaaaacc aactaaatct aagactagga cagggccctc     29040
tttttataaa ctcagcccac aacttggata ttaactacaa caaaggcctt tacttgttta     29100
cagcttcaaa caattccaaa agcttgagg  ttaacctaag cactgccaag gggttgatgt     29160
ttgacgctac agccatagcc attaatgcag gagatgggct tgaatttggt tcacctaatg     29220
caccaaacac aaatccctc  aaaacaaaaa ttggccatgg cctagaattt gattcaaaca     29280
aggctatggt tcctaaacta ggaactggcc ttagttttga cagcacaggt gccattacag     29340
taggaaacaa aaataatgat aagctaactt tgtggaccac accagctcca tctcctaact     29400
gtagactaaa tgcagagaaa gatgctaaac tcactttggt cttaacaaaa tgtggcagtc     29460
aaatacttgc tacagtttca gttttggctg ttaaaggcag tttggctcca atatctggaa     29520
cagttcaaag tgctcatctt attataagat ttgacgaaaa tggagtgcta ctaaacaatt     29580
ccttcctgga cccagaatat tggaacttta gaaatggaga tcttactgaa ggcacagcct     29640
atacaaacgc tgttggattt atgcctaacc tatcagctta tccaaaatct cacggtaaaa     29700
```

```
ctgccaaaag taacattgtc agtcaagttt acttaaacgg agacaaaact aaacctgtaa    29760
cactaaccat tacactaaac ggtacacagg aaacaggaga cacaactcca agtgcatact    29820
ctatgtcatt tcatgggac tggtctggcc acaactacat taatgaaata tttgccacat     29880
cctcttacac tttttcatac attgcccaag aataaagaat cgtttgtgtt atgtttcaac    29940
gtgtttattt ttcaattgcc cgggatcggt gatcaccgat ccagacatga taagatacat    30000
tgatgagttt ggacaaacca caactagaat gcagtgaaaa aaatgcttta tttgtgaaat    30060
ttgtgatgct attgctttat ttgtaaccat tataagctgc aataaacaag ttcccggatc    30120
gcgatccggc ccgaggctgt agccgacgat ggtgcgccag gagagttgtt gattcattgt    30180
ttgcctccct gctgcggttt ttcaccgaag ttcatgccag tccagcgttt ttgcagcaga    30240
aaagccgccg acttcggttt gcggtcgcga gtgaagatcc ctttcttgtt accgccaacg    30300
cgcaatatgc cttgcgaggt cgcaaaatcg gcgaaattcc atacctgttc accgacgacg    30360
gcgctgacgc gatcaaagac gcggtgatac atatccagcc atgcacactg atactcttca    30420
ctccacatgt cggtgtacat tgagtgcagc ccggctaacg tatccacgcc gtattcggtg    30480
atgataatcg gctgatgcag tttctcctgc caggccagaa gttcttttc cagtaccttc      30540 tctgccgttt ccaaatcgcc gctttggaca taccatccgt aataacggtt caggcacagc    30600
acatcaaaga gatcgctgat ggtatcggtg tgagcgtcgc agaacattac attgacgcag    30660
gtgatcggac gcgtcgggtc gagtttacgg gttgcttccg ccagtggcgc gaaatattcc    30720
cgtgcacctt gcggacgggt atccggttcg ttggcaatac tccacatcac cacgcttggg    30780 tggttttgt cacgcgctat cagctcttta atcgcctgta agtgcgcttg ctgagtttcc     30840
ccgttgactg cctcttcgct gtacagttct ttcggcttgt gcccgcttc gaaaccaatg     30900 cctaaagaga ggttaaagcc gacagcagca gtttcatcaa tcaccacgat gccatgttca    30960
tctgcccagt cgagcatctc ttcagcgtaa gggtaatgcg aggtacggta ggagttggcc    31020
ccaatccagt ccattaatgc gtggtcgtgc accatcagca cgttatcgaa tcctttgcca    31080
cgcaagtccg catcttcatg acgaccaaag ccagtaaagt agaacggttt gtggttaatc    31140
aggaactgtt cgcccttcac tgccactgac cggatgccga cgcgaagcgg gtagatatca    31200
cactctgtct ggcttttggc tgtgacgcac agttcataga gataaccttc acccggttgc    31260
cagaggtgcg gattcaccac ttgcaaagtc ccgctagtgc cttgtccagt tgcaaccacc    31320
tgttgatccg catcacgcag ttcaacgctg acatcaccat tggccaccac ctgccagtca    31380
acagacgcgt ggttacagtc ttgcgcgaca tgcgtcacca cggtgatatc gtccacccag    31440
gtgttcggcg tggtgtagag cattacgctg cgatggattc cggcatagtt aaagaaatca    31500
tggaagtaag actgcttttt cttgccgttt tcgtcggtaa tcaccattcc cggcgggata    31560
gtctgccagt tcagttcgtt gttcacacaa acggtgatac gtacttttt cccggcaata    31620 acatacggcg tgacatcggc ttcaaatggc gtatagccgc cctgatgctc catcacttcc    31680
tgattattga cccacacttt gccgtaatga gtgaccgcat cgaaacgcag cacgatacgc    31740
tggcctgccc aacctttcgg tataaagact tcgcgctgat accagacgtt gcccgcataa    31800
ttacgaatat ctgcatcggc gaactgatcg ttaaaactgc ctggcacagc aattgcccgg    31860 cttcttgta acgcgctttc ccaccaacgc tgatcaattc cacagttttc gcgatccaga     31920
ctgaatgccc acaggccgtc gagttttttg atttcacggg ttggggtttc tacaggacgg    31980
accatgcgtt cgacctttct cttctttttt gggcccatga tggcagatcc gtatagtgag    32040
tcgtattagc tggttctttc cgcctcagaa gccatagagc ccaccgcatc cccagcatgc    32100
```

-continued

```
ctgctattgt cttcccaatc ctcccccttg ctgtcctgcc ccaccccacc ccccagaata    32160
gaatgacacc tactcagaca atgcgatgca atttcctcat tttattagga aaggacagtg    32220
ggagtggcac cttccagggt caaggaaggc acggggagg ggcaaacaac agatggctgg    32280
caactagaag gcacagtcga ggctgatcag cgagctctag atgcatgctc gagcggccgc    32340
cagtgtgatg gatatctgca gaattccagc acactggcgg ccgttactag tggatccgag    32400
ctcggtaccc ggccgttata acaccactcg acacggcacc agctcaatca gtcacagtgt    32460
aaaaaagggc caagtgcaga gcgagtatat ataggactaa aaaatgacgt aacggttaaa    32520
gtccacaaaa aacacccaga aaaccgcacg cgaacctacg cccagaaacg aaagccaaaa    32580
aacccacaac ttcctcaaat cgtcacttcc gttttcccac gttacgtcac ttcccatttt    32640
aagaaaacta caattcccaa cacatacaag ttactccgcc ctaaaaccta cgtcacccgc    32700
cccgttccca cgccccgcgc cacgtcacaa actccacccc ctcattatca tattggcttc    32760
aatccaaaat aaggtatatt attgatgatg ggtcgtta                            32798
```

<210> SEQ ID NO 2
<211> LENGTH: 465
<212> TYPE: DNA
<213> ORGANISM: DNA encoding tumor necrosis factor-alpha
<220> FEATURE:
<221> NAME/KEY: misc_feature
<223> OTHER INFORMATION: SEQ ID NO:2 represents the nucleotides of
      positions 1469 through 1933 of SEQ ID NO:1

<400> SEQUENCE: 2

```
tcatcttctc gaacccgag tgacaagcct gtagcccatg ttgtagcaaa ccctcaagct      60
gaggggcagc tccagtggct gaaccgccgg gccaatgccc tcctggccaa tggcgtggag    120
ctgagagata accagctggt ggtgccatca gagggcctgt acctcatcta ctcccaggtc    180
ctcttcaagg gccaaggctg cccctccacc catgtgctcc tcacccacac catcagccgc    240
atcgccgtct cctaccagac caaggtcaac ctcctctctg ccatcaagag ccctgccag     300 agggagaccc cagagggggc tgaggccaag ccctggtatg agcccatcta tctgggaggg    360
gtcttccagc tggagaaggg tgaccgactc agcgctgaga tcaatcggcc cgactatctc    420
gactttgccg agtctgggca ggtctacttt gggatcattg ccctg                    465
```